United States Patent
Sharma

(10) Patent No.: US 10,561,423 B2
(45) Date of Patent: Feb. 18, 2020

(54) CARDIAC SHUNT DEVICE AND DELIVERY SYSTEM

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 212 days.

(21) Appl. No.: 15/868,126

(22) Filed: Jan. 11, 2018

(65) Prior Publication Data

US 2019/0015103 A1    Jan. 17, 2019

Related U.S. Application Data

(63) Continuation-in-part of application No. 15/605,286, filed on May 25, 2017, now Pat. No. 10,154,844.

(Continued)

(51) Int. Cl.
*A61B 17/11* (2006.01)
*A61B 17/00* (2006.01)

(52) U.S. Cl.
CPC ....... *A61B 17/11* (2013.01); *A61B 2017/0034* (2013.01); *A61B 2017/00243* (2013.01);
(Continued)

(58) Field of Classification Search
CPC ... A61B 17/11; A61B 17/122; A61B 17/1227; A61B 2017/00247; A61B 2017/0034;
(Continued)

(56) References Cited

U.S. PATENT DOCUMENTS

| 4,401,045 A | 8/1983 | Russell |
| 4,551,660 A | 11/1985 | Suzuki |

(Continued)

FOREIGN PATENT DOCUMENTS

| EP | 0123359 B1 | 3/1989 |
| EP | 0326757 B1 | 7/1993 |

(Continued)

OTHER PUBLICATIONS

"Choledochojejunostomy with an innovative magnetic compressive anastomosis: How to determine optimal pressure?" Fei Xue et al. World J Gastroenterol Feb. 21, 2016; 22(7): 2326-2335.

(Continued)

*Primary Examiner* — Ryan J. Severson
*Assistant Examiner* — Mohamed G Gabr
(74) *Attorney, Agent, or Firm* — Novel IP

(57) ABSTRACT

A shunt device for creating a shunt in an atrial septum includes magnets coupled to inner loops of a coil comprising at least two inner loops and two outer loops, with a diameter of each of the inner loops being less than a diameter of the outer loops. The coil is made of a shape memory alloy (SMA) and is adapted to exert a compressive force upon layers of tissue caught between the inner loops of the coil. The magnets are adapted to provide additional compressive force to adjacent inner loops of the coil, thereby further causing the coil to cut through the layers of tissue and create a shunt. The diameter of the resultant shunt is less than the diameter of the outer loops, thereby preventing the outer two loops from passing through the created shunt. At least one end of the coil has a connection means for connecting with a delivery device.

4 Claims, 19 Drawing Sheets

Related U.S. Application Data

(60) Provisional application No. 62/425,951, filed on Nov. 23, 2016, provisional application No. 62/408,795, filed on Oct. 16, 2016, provisional application No. 62/366,185, filed on Jul. 25, 2016, provisional application No. 62/444,995, filed on Jan. 11, 2017.

(52) U.S. Cl.
CPC .............. *A61B 2017/00867* (2013.01); *A61B 2017/00876* (2013.01); *A61B 2017/1107* (2013.01); *A61B 2017/1139* (2013.01)

(58) Field of Classification Search
CPC ........... A61B 2017/00477; A61B 2017/00783; A61B 2017/00867; A61B 2017/00876; A61B 2017/0649; A61B 2017/1107; A61B 2017/1139
See application file for complete search history.

(56) References Cited

U.S. PATENT DOCUMENTS

| | | | |
|---|---|---|---|
| 4,698,609 A | 10/1987 | Goehle | |
| 4,899,744 A | 2/1990 | Fujitsuka | |
| 5,595,562 A | 1/1997 | Grier | |
| 5,631,613 A | 5/1997 | Niimi | |
| 5,660,487 A | 8/1997 | Cayzer | |
| 5,690,656 A | 11/1997 | Cope | |
| 6,171,320 B1 | 1/2001 | Monassevitch | |
| 6,217,339 B1 | 4/2001 | Tsubata | |
| 6,352,543 B1 | 3/2002 | Cole | |
| 6,402,765 B1 | 6/2002 | Monassevitch | |
| 6,517,556 B1 | 2/2003 | Monassevitch | |
| 6,565,581 B1 | 5/2003 | Spence | |
| 6,652,540 B1 | 11/2003 | Cole | |
| 6,719,768 B1 | 4/2004 | Cole | |
| 6,802,847 B1 | 10/2004 | Carson | |
| 6,884,250 B2 | 4/2005 | Monassevitch | |
| 6,896,684 B2 | 5/2005 | Monassevitch | |
| 6,932,827 B2 | 8/2005 | Cole | |
| 7,094,247 B2 | 8/2006 | Monassevitch | |
| 7,222,428 B2 | 5/2007 | Koike | |
| 7,232,449 B2 | 6/2007 | Sharkawy | |
| 7,241,300 B2 | 7/2007 | Sharkawy | |
| 7,282,057 B2 | 10/2007 | Surti | |
| 7,374,153 B2 | 5/2008 | Huang | |
| 7,393,027 B1 | 7/2008 | Chen | |
| 7,431,727 B2 | 10/2008 | Cole | |
| 7,527,185 B2 | 5/2009 | Harari | |
| 7,618,427 B2 | 11/2009 | Ortiz | |
| 7,635,374 B2 | 12/2009 | Monassevitch | |
| 7,728,707 B2 | 6/2010 | Gilardi | |
| 7,892,244 B2 | 2/2011 | Monassevitch | |
| 7,909,837 B2 | 3/2011 | Crews | |
| 7,938,841 B2 | 5/2011 | Sharkawy | |
| 8,118,821 B2 | 2/2012 | Mouw | |
| 8,142,454 B2 | 3/2012 | Harrison | |
| 8,205,782 B2 | 6/2012 | Harari | |
| 8,262,680 B2 | 9/2012 | Swain | |
| 8,518,062 B2 | 8/2013 | Cole | |
| 8,556,919 B2 | 10/2013 | Aguirre | |
| 8,623,036 B2 | 1/2014 | Harrison | |
| 8,628,548 B2 | 1/2014 | Aguirre | |
| 8,629,572 B1 | 1/2014 | Phillips | |
| 8,679,139 B2 | 3/2014 | Aguirre | |
| 8,685,046 B2 | 4/2014 | Viola | |
| 8,728,105 B2 | 5/2014 | Aguirre | |
| 8,764,773 B2 | 7/2014 | Harari | |
| 8,828,031 B2 | 9/2014 | Fox | |
| 8,828,032 B2 | 9/2014 | McWeeney | |
| 8,845,663 B2 | 9/2014 | Chmura | |
| 8,864,781 B2 | 10/2014 | Surti | |
| 8,870,898 B2 | 10/2014 | Beisel | |
| 8,870,899 B2 | 10/2014 | Beisel | |
| 8,876,699 B2 | 11/2014 | Sato | |
| 8,910,366 B2 | 12/2014 | Fuse | |
| 8,920,446 B2 | 12/2014 | Viola | |
| 8,946,919 B2 | 2/2015 | Phillips | |
| 8,946,920 B2 | 2/2015 | Phillips | |
| 9,168,041 B2 | 10/2015 | Zaritsky | |
| 9,205,236 B2 | 12/2015 | McNamara | |
| 9,226,753 B2 | 1/2016 | Surti | |
| 9,232,997 B2 | 1/2016 | Sugimoto | |
| 9,240,710 B2 | 1/2016 | Kawarai | |
| 9,277,995 B2 | 3/2016 | Celermajer | |
| 9,332,990 B2 | 5/2016 | Requarth | |
| 9,358,371 B2 | 6/2016 | McNamara | |
| 9,364,238 B2 | 6/2016 | Bakos | |
| 9,456,812 B2 | 10/2016 | Finch | |
| 9,492,173 B2 | 11/2016 | McWeeney | |
| 2002/0183768 A1 | 12/2002 | Deem | |
| 2003/0014061 A1 | 1/2003 | Houser | |
| 2003/0153932 A1 | 8/2003 | Spence | |
| 2003/0229363 A1 | 12/2003 | Sharkawy | |
| 2004/0034377 A1 | 2/2004 | Sharkawy | |
| 2004/0059280 A1 | 3/2004 | Makower | |
| 2004/0102794 A1 | 5/2004 | Roy | |
| 2004/0116945 A1 | 6/2004 | Sharkawy | |
| 2004/0215214 A1 | 10/2004 | Crews | |
| 2004/0260393 A1* | 12/2004 | Rahdert | A61B 17/00234 623/2.36 |
| 2005/0080439 A1 | 4/2005 | Carson | |
| 2006/0111733 A1 | 5/2006 | Shriver | |
| 2006/0271107 A1 | 11/2006 | Harrison | |
| 2006/0282106 A1 | 12/2006 | Cole | |
| 2007/0118158 A1 | 5/2007 | Deem | |
| 2007/0213748 A1 | 9/2007 | Deem | |
| 2007/0250084 A1 | 10/2007 | Sharkawy | |
| 2008/0114384 A1 | 5/2008 | Chang | |
| 2008/0200934 A1 | 8/2008 | Fox | |
| 2008/0208224 A1 | 8/2008 | Surti | |
| 2008/0300609 A1 | 12/2008 | Tabet | |
| 2009/0048618 A1 | 2/2009 | Harrison | |
| 2009/0125042 A1 | 5/2009 | Mouw | |
| 2009/0227828 A1 | 9/2009 | Swain | |
| 2010/0025605 A1 | 2/2010 | Galtz | |
| 2010/0036399 A1 | 2/2010 | Viola | |
| 2010/0049223 A1 | 2/2010 | Granja Filho | |
| 2010/0179510 A1 | 7/2010 | Fox | |
| 2010/0256659 A1 | 10/2010 | Aguirre | |
| 2010/0292729 A1 | 11/2010 | Aguirre | |
| 2010/0318015 A1 | 12/2010 | Kassab | |
| 2010/0331862 A1 | 12/2010 | Monassevitch | |
| 2011/0054498 A1 | 3/2011 | Monassevitch | |
| 2011/0087252 A1 | 4/2011 | Chmura | |
| 2011/0112559 A1 | 5/2011 | Monassevitch | |
| 2011/0118765 A1 | 5/2011 | Aguirre | |
| 2011/0144560 A1 | 6/2011 | Gagner | |
| 2011/0160752 A1 | 6/2011 | Aguirre | |
| 2011/0184505 A1 | 7/2011 | Sharkawy | |
| 2011/0295285 A1 | 12/2011 | McWeeney | |
| 2012/0035628 A1 | 2/2012 | Aguirre | |
| 2012/0150092 A1 | 6/2012 | McAllister | |
| 2012/0172782 A1 | 7/2012 | Thompson | |
| 2012/0197061 A1 | 8/2012 | Requarth | |
| 2012/0197062 A1 | 8/2012 | Requarth | |
| 2012/0259350 A1 | 10/2012 | Gagner | |
| 2012/0324975 A1 | 12/2012 | Anderson | |
| 2012/0330330 A1 | 12/2012 | Gagner | |
| 2013/0110141 A1 | 5/2013 | Chmura | |
| 2013/0226205 A1 | 8/2013 | Zaritsky | |
| 2013/0253548 A1 | 9/2013 | Harrison | |
| 2013/0253550 A1 | 9/2013 | Beisel | |
| 2013/0325042 A1 | 12/2013 | Fabian | |
| 2014/0100423 A1 | 4/2014 | Monassevitch | |
| 2014/0236064 A1 | 8/2014 | Binmoeller | |
| 2014/0236200 A1 | 8/2014 | Beisel | |
| 2014/0309669 A1 | 10/2014 | Fabian | |
| 2014/0309670 A1 | 10/2014 | Bakos | |
| 2014/0343583 A1 | 11/2014 | McWeeney | |
| 2014/0364881 A1 | 12/2014 | Meron | |
| 2014/0379011 A1 | 12/2014 | Viola | |
| 2015/0057687 A1 | 2/2015 | Gittard | |

(56) References Cited

U.S. PATENT DOCUMENTS

| | | |
|---|---|---|
| 2015/0057688 A1 | 2/2015 | Beisel |
| 2015/0164508 A1 | 6/2015 | Hernandez |
| 2015/0182224 A1 | 7/2015 | Altman |
| 2015/0222165 A1 | 8/2015 | Filippa |
| 2016/0022266 A1 | 1/2016 | Lukin |
| 2016/0120550 A1 | 5/2016 | McNamara |
| 2016/0262761 A1 | 9/2016 | Beisel |
| 2016/0324523 A1 | 11/2016 | Lukin |
| 2017/0119394 A1 | 5/2017 | McWeeney |

FOREIGN PATENT DOCUMENTS

| | | |
|---|---|---|
| EP | 0754434 B1 | 9/1999 |
| EP | 1284660 A1 | 2/2003 |
| EP | 1307144 A1 | 5/2003 |
| EP | 1077047 B1 | 7/2003 |
| EP | 0910298 B1 | 8/2003 |
| EP | 1389984 A1 | 2/2004 |
| EP | 1435824 A2 | 7/2004 |
| EP | 1435856 A1 | 7/2004 |
| EP | 1435872 A2 | 7/2004 |
| EP | 0954248 B1 | 9/2004 |
| EP | 1550415 A2 | 7/2005 |
| EP | 1334696 B1 | 3/2007 |
| EP | 1938009 A1 | 7/2008 |
| EP | 1551313 B1 | 10/2008 |
| EP | 1301129 B1 | 9/2009 |
| EP | 2131752 A1 | 12/2009 |
| EP | 2151199 A1 | 2/2010 |
| EP | 1289428 B1 | 3/2010 |
| EP | 2236242 A1 | 10/2010 |
| EP | 1732473 B1 | 12/2010 |
| EP | 2258317 A2 | 12/2010 |
| EP | 2124759 B1 | 6/2011 |
| EP | 2332473 A1 | 6/2011 |
| EP | 2207488 B1 | 9/2012 |
| EP | 2519164 A1 | 11/2012 |
| EP | 2429625 B1 | 5/2013 |
| EP | 2086426 B1 | 7/2013 |
| EP | 2413813 B1 | 8/2013 |
| EP | 2632346 A2 | 9/2013 |
| EP | 2690767 A1 | 1/2014 |
| EP | 2485657 B1 | 8/2014 |
| EP | 2839796 A1 | 2/2015 |
| EP | 2424472 B1 | 12/2015 |
| EP | 2958527 A1 | 12/2015 |
| EP | 2967867 A1 | 1/2016 |
| EP | 2537490 B1 | 8/2016 |
| WO | 1997013463 A1 | 4/1997 |
| WO | 1998016161 A1 | 4/1998 |
| WO | 2001082803 A1 | 11/2001 |
| WO | 2002013704 A1 | 2/2002 |
| WO | 2002096327 A2 | 12/2002 |
| WO | 2003024307 A2 | 3/2003 |
| WO | 2003101311 A1 | 12/2003 |
| WO | 2003103510 A1 | 12/2003 |
| WO | 2004008937 A2 | 1/2004 |
| WO | 2004045383 A2 | 6/2004 |
| WO | 2004105693 A2 | 12/2004 |
| WO | 2005027736 A2 | 3/2005 |
| WO | 2005094334 A2 | 10/2005 |
| WO | 2006127236 A2 | 11/2006 |
| WO | 2007042016 A1 | 4/2007 |
| WO | 2007140557 A2 | 12/2007 |
| WO | 2007140562 A2 | 12/2007 |
| WO | 2008061024 A2 | 5/2008 |
| WO | 2008101077 A1 | 8/2008 |
| WO | 2008106279 A1 | 9/2008 |
| WO | 2009048954 A1 | 4/2009 |
| WO | 2009081948 A1 | 7/2009 |
| WO | 2010115116 A1 | 10/2010 |
| WO | 2010132356 A1 | 11/2010 |
| WO | 2011008988 A1 | 1/2011 |
| WO | 2011062831 A1 | 5/2011 |
| WO | 2011081988 A1 | 7/2011 |
| WO | 2011085006 A2 | 7/2011 |
| WO | 2012007042 A1 | 1/2012 |
| WO | 2012007052 A1 | 1/2012 |
| WO | 2012009431 A2 | 1/2012 |
| WO | 2012170502 A1 | 12/2012 |
| WO | 2013009886 A1 | 1/2013 |
| WO | 2013143495 A1 | 10/2013 |
| WO | 2013170474 A1 | 11/2013 |
| WO | 2013176993 A1 | 11/2013 |
| WO | 2014055193 A1 | 4/2014 |
| WO | 2014070720 A1 | 5/2014 |
| WO | 2014130850 A1 | 8/2014 |
| WO | 2014172194 A1 | 10/2014 |
| WO | 2015103346 A1 | 7/2015 |
| WO | 2015191859 A2 | 12/2015 |
| WO | 2015192022 A1 | 12/2015 |
| WO | 2016007917 A2 | 1/2016 |
| WO | 2016014644 A1 | 1/2016 |
| WO | 2016014821 A1 | 1/2016 |

OTHER PUBLICATIONS

"Understanding gastric forces calculated from high-resolution pill tracking" Laulicht et al. Proceedings of the National Academy of Scienes of the United States of America, May 4, 2010; vol. 107, No. 18: 8201-8206.

Cronin et al., "Normal small bowel wall characteristics on MR enterography"; European Journal of Radiology 75 (2010) 207-211.

Mesenas et al., "Duodenal EUS to identify thickening of the extrahepatic biliary tree wall in primary sclerosing cholangitis"; Gastrointestinal Endoscopy vol. 63, No. 3: 2006, pp. 403-408.

Rapaccini, et al., "Gastric Wall Thickness in Normal and Neoplastic Subjects: A Prospective Study Performed by Abdominal Ultrasound"; Gastrointestinal Radiology 13: 197-199 (1998).

Shikata, et al., "Experimental Studies on the Hemodynamics of the Small Intestine Following Increased Intraluminal Pressure"; Surgery, Gynecology & Obstetrics: Feb. 1983, vol. 156, pp. 155-160.

Matcuk et al.; "Ultrasound Measurements of the Bile Ducts and Gallbladder"; Ultrasound Quarterly, vol. 30, No. 1, Mar. 2014, pp. 41-48.

International Search Report for PCT/US2017/034475, dated Sep. 1, 2017.

* cited by examiner

702 — In order to form a shunt between a first chamber and a second chamber of a heart, firstly, a wall/septum between the two chambers is identified 704 — The septum between the identified chambers is pierced by using a needle encased in a catheter positioned in the right heart chamber to obtain a trans-septal puncture 706 — A coiled SMA wire having magnets threaded on adjacent inner loops and not on outer loops, where the diameter of outer loops is greater than that of inner loops, is deployed through the trans-septal puncture, such that approximately half of the coil is in the first chamber and approximately the other half is in the second chamber 708 — During deployment, the SMA wire changes from a substantially linear pre-deployment shape to a coiled post-deployment shape 710 — The inner loops of the coil compress due to the attractive forces between the magnets, causing pressure necrosis, and slowly cut through the septum forming a septal defect between the first and the second chambers of the heart 712 — The large diameter outer coil loops without the magnets anchor the coil in the septal defect preventing the coil from passing spontaneously or dislodging

FIG. 7

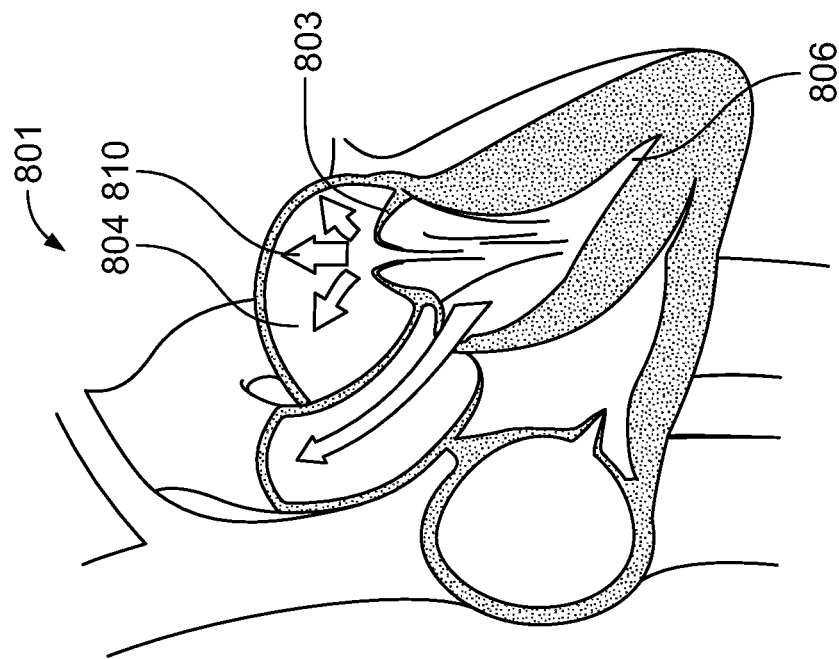
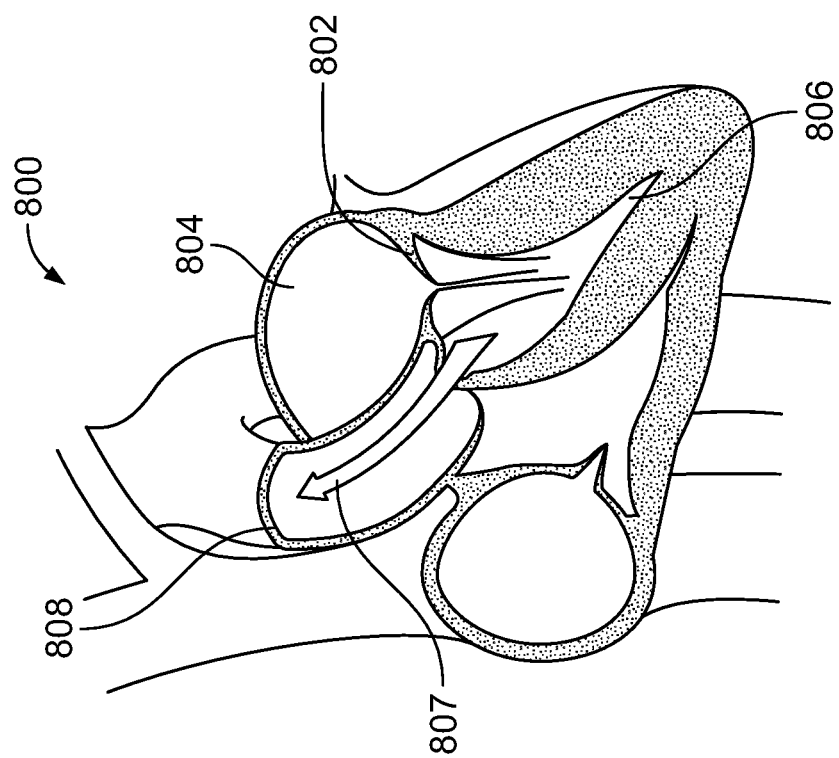

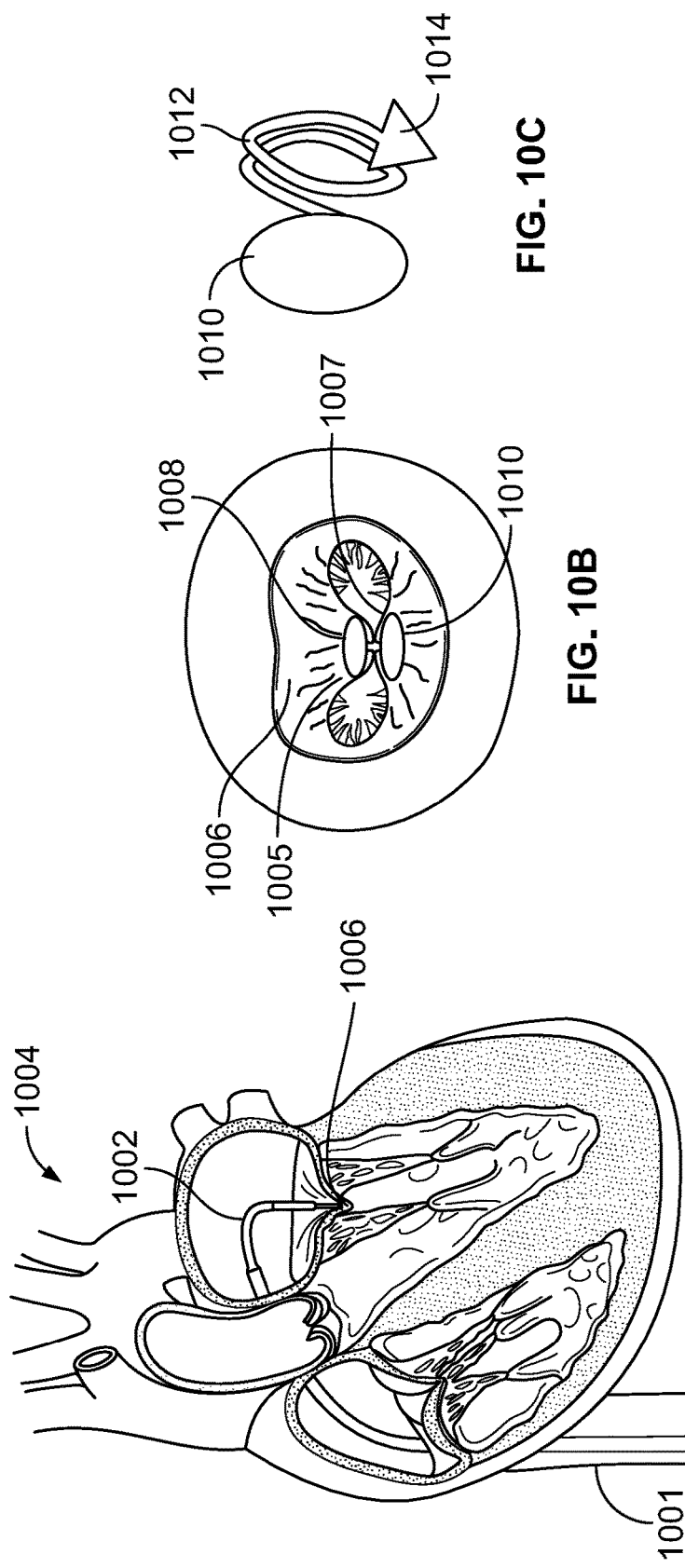

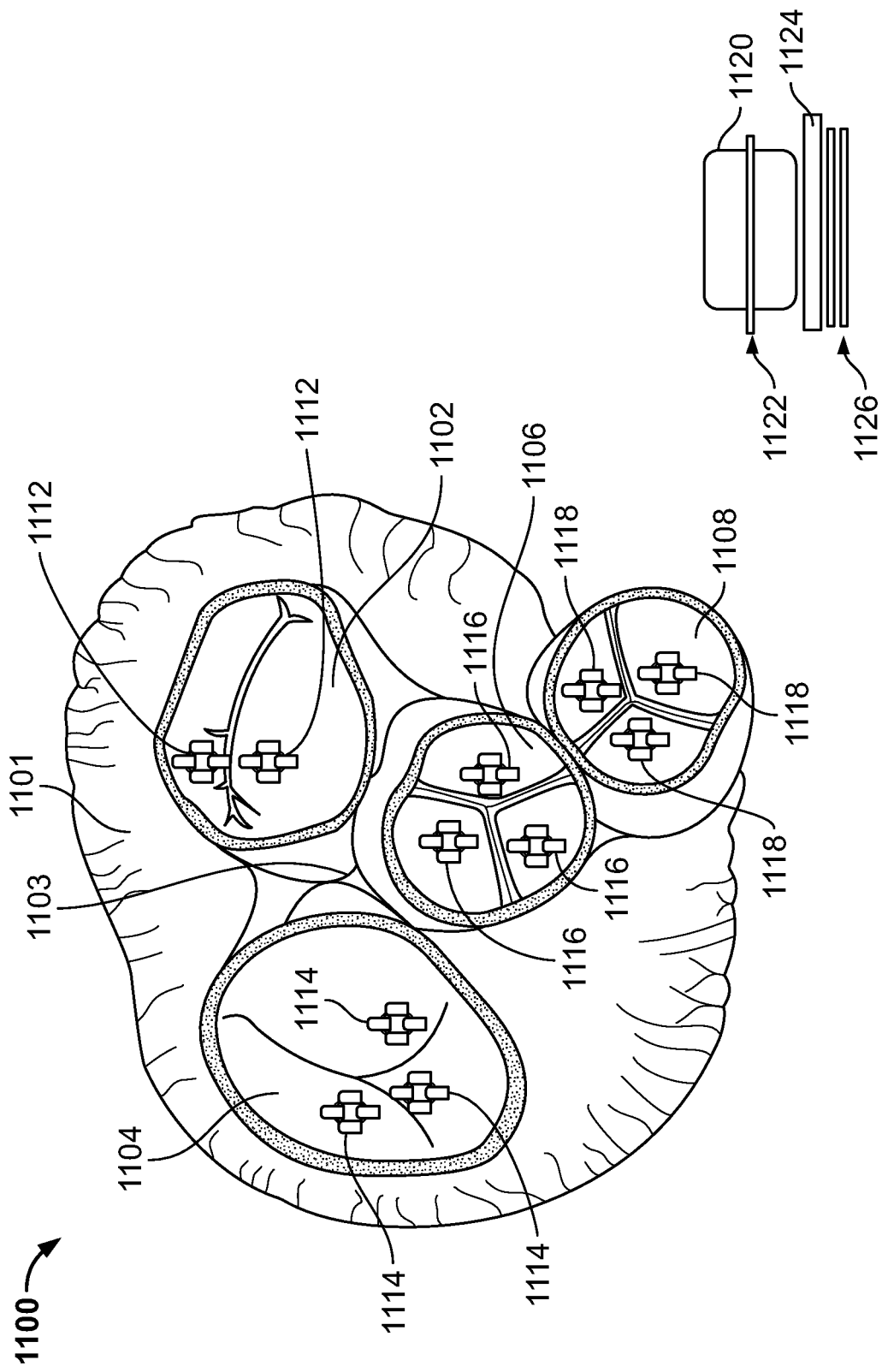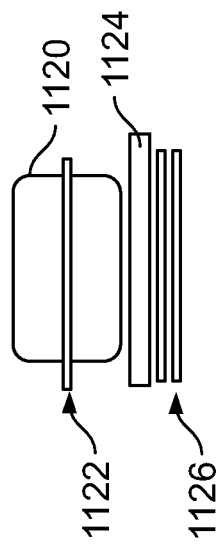
FIG. 11A
FIG. 11B

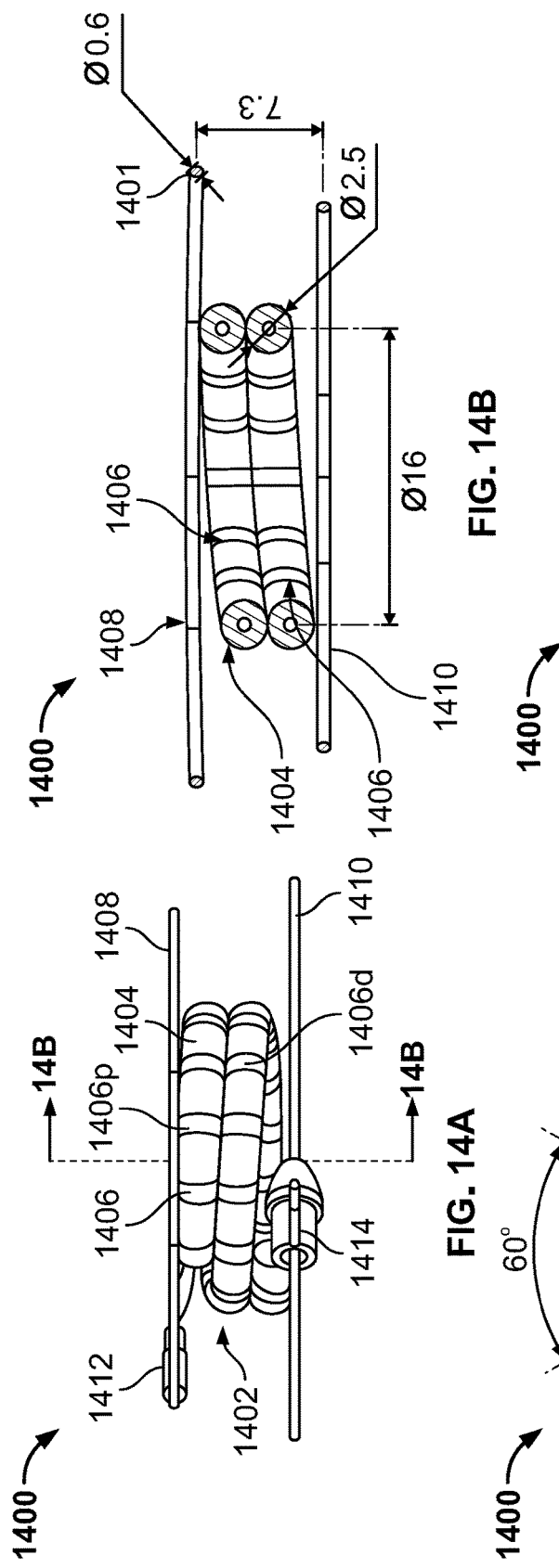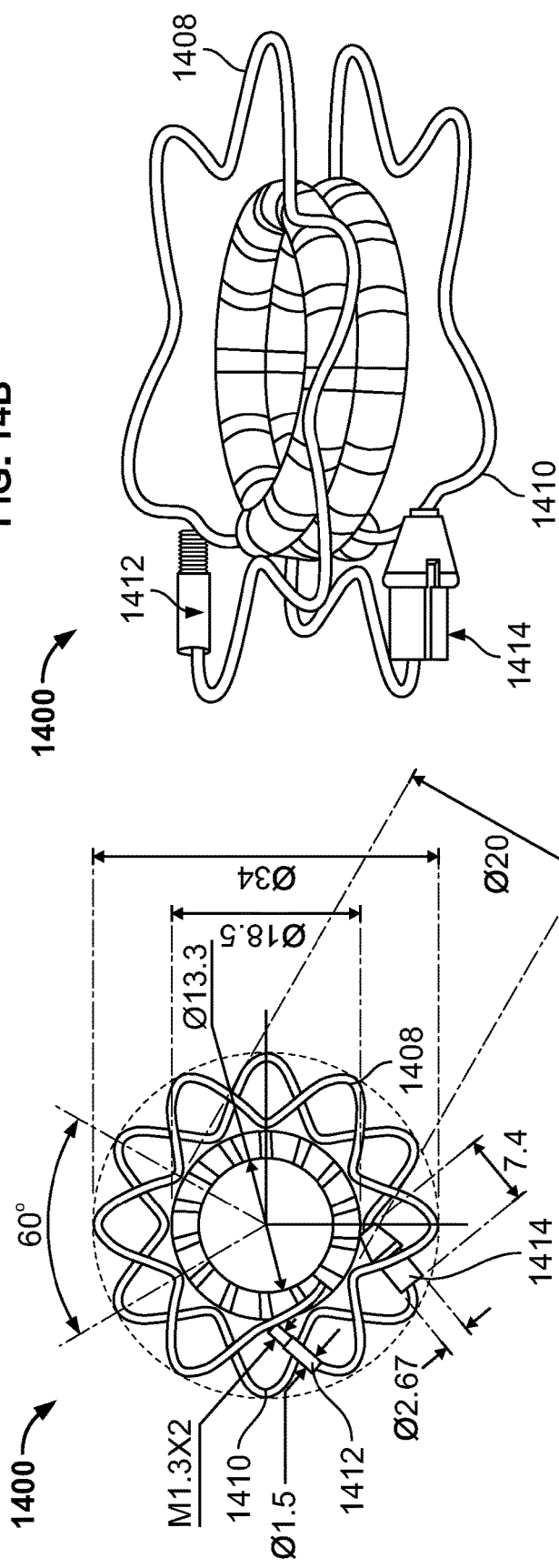

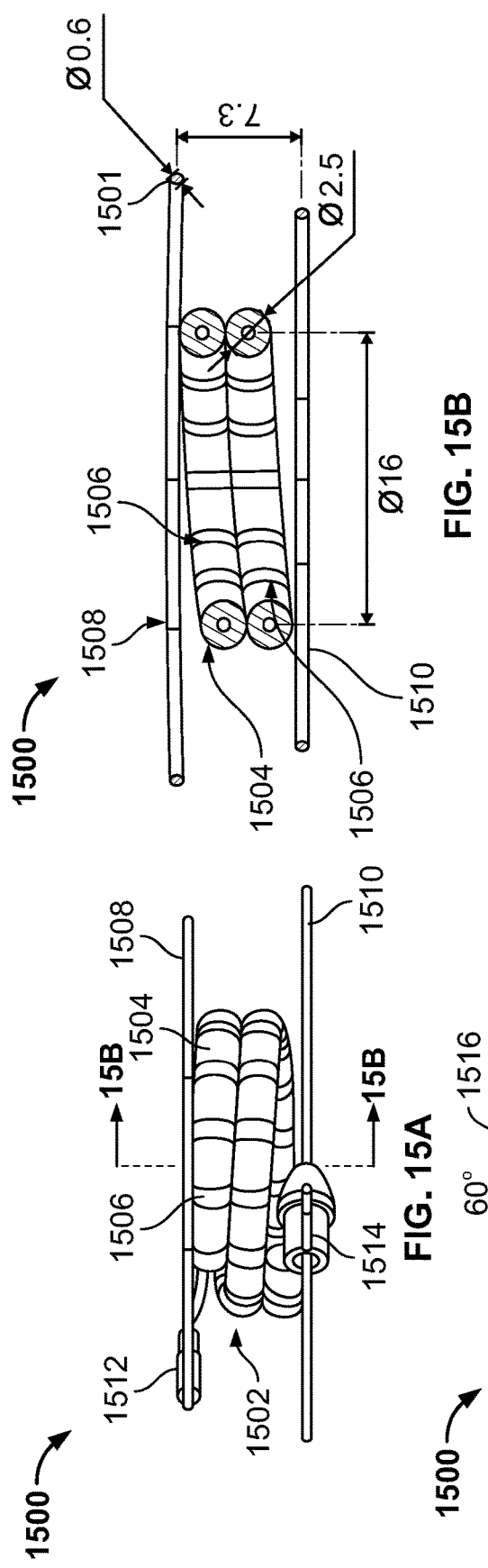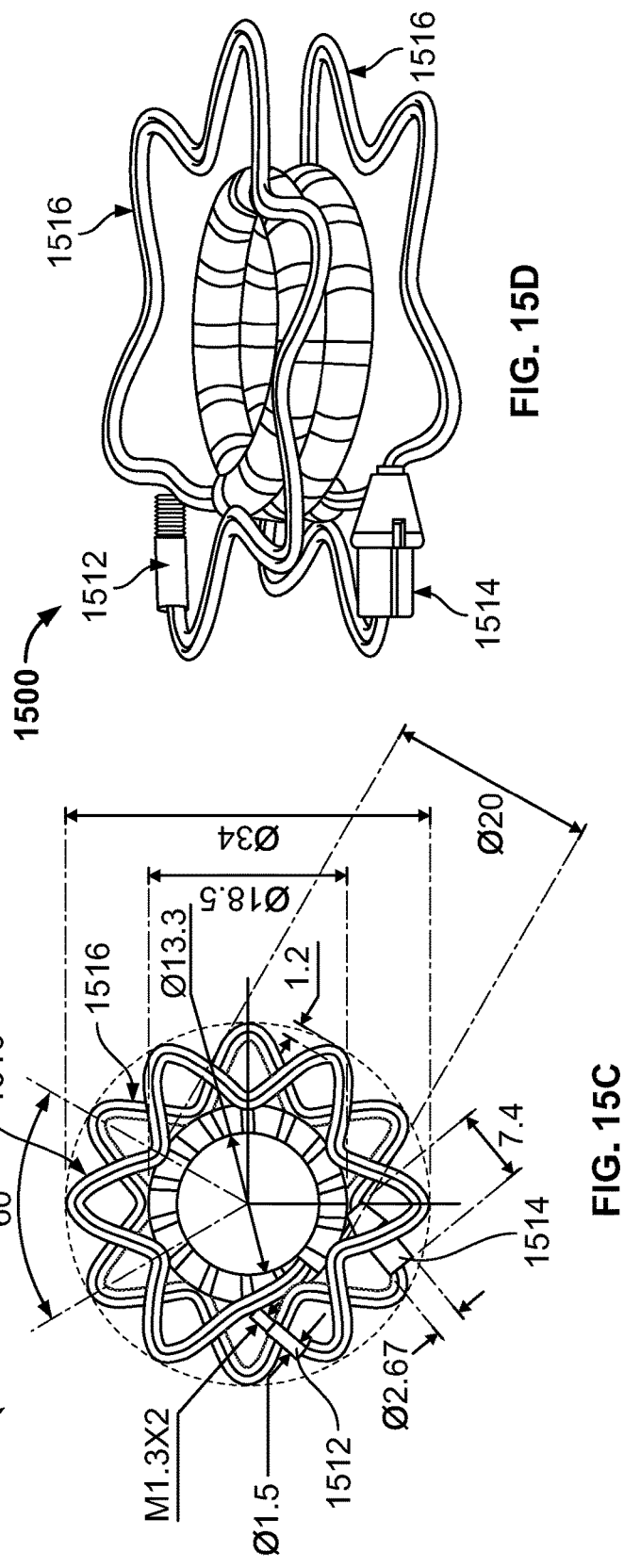

CARDIAC SHUNT DEVICE AND DELIVERY SYSTEM

CROSS-REFERENCE

The present application is a continuation in part of U.S. patent application Ser. No. 15/605,286, entitled "Magnetic Anastomosis Device and Delivery System" and filed on May 25, 2017, for priority, which is herein incorporated by reference in its entirety. The '286 Application further relies on, for priority, U.S. Patent Provisional Application No. 62/425,951, entitled "Anastomosis Device and Delivery System", filed on Nov. 23, 2016, U.S. Patent Provisional Application No. 62/408,795, entitled "Anastomosis Device and Delivery System", filed on Oct. 16, 2016, and U.S. Patent Provisional Application No. 62/366,185, entitled "Anastomosis Device and Delivery System", filed on Jul. 25, 2016, all of which are incorporated herein by reference in their entirety.

The present application also relies on U.S. Provisional Patent Application No. 62/444,995, entitled "Cardiac Anastomosis Device and Delivery System" and filed on Jan. 11, 2017, for priority, which is herein incorporated by reference in its entirety.

FIELD

The present specification is directed toward formation of shunts in human bodies and, more specifically, to a device which uses magnetic compression to create a shunt in a human body and a delivery system for deploying the device at a desired location within the body. The present specification is also directed toward controlling the flow of bodily fluids through a body valve and, more specifically, toward using magnets to control the flow through said valve.

BACKGROUND

In cases of heart disease, such as one which requires decompression of one of the chambers of the heart, e.g. the left atrium or right atrium, a septal defect or shunt is created in the septum/wall between the two heart chambers to allow for the flow of blood from the high-pressure chamber to the low-pressure chamber, thus decompressing the high pressure chamber. Most of these procedures are performed surgically or by using non-removable metal stem-like devices.

Prior art devices for creating shunts often comprise a piercing tip which can be hazardous and cause injury to adjacent organs. Additionally, most of the prior art techniques create the shunt instantaneously, causing sudden increase in pressure and work-load on a portion of the heart which could result in acute heart failure. Also, most prior art devices are permanently implanted, creating the need for long-term antiplatelet and anti-coagulant medication to prevent clot formation. These medications increase the risk of life-threatening conditions such as bleeding or stroke.

Hence, what is needed is an efficient and small shunt device which may be delivered with ease within a human body for slowly creating a shunt over a period of time, resulting in a slow decompression of the high-pressure system and in turn, a slow increase in pressure and work-load in the low-pressure system. What is also needed is a shunt device which can be removed safely after the shunt is formed, obviating the need for long-term anticoagulant or antiplatelet medications. Further, there is need for a shunt device which exerts a sufficiently high compressive force on an organ wall to create a shunt, yet retains a small enough profile to be delivered through a minimally invasive delivery device, such as a catheter. There is also a need for a shunt device that does not rely solely on magnetic forces for correct orientation and positioning inside the human body.

Prior art devices for controlling valve function, specifically preventing the back-flow or leakage of fluid, create a fixed restriction which impedes the forward flow as well as restricting the backward flow, thereby increasing the pressure on the heart, and in turn, increasing the work-load.

Hence, what is also needed is an efficient and small device which may be delivered with ease within a human body and which dynamically controls the flow of fluid across a valvular structure. What is also needed is a device that controls the flow of fluid in one direction preferentially over the opposite direction, thereby augmenting or restoring the normal valvular function of a valve. What is also needed is a valve control device which can be removed safely.

SUMMARY

The present specification discloses a shunt device for creating a shunt in an atrial septum of a patient, comprising: a wire comprised of a shape memory alloy, wherein the wire is adapted to transform from a substantially straight wire to a coil shape upon heating and wherein the wire, upon transforming to the coil shape, comprises at least two inner loops and at least two outer loops, wherein a diameter of the at least two inner loops are each less than a diameter of each of the at least two outer loops, and wherein the wire, when in the coil shape, is adapted to exert a compressive force upon layers of tissue caught between the at least two inner loops; and a plurality of magnets coupled to the at least two inner loops, wherein the plurality of magnets are adapted to provide a compressive force to adjacent inner loops of the wire in the coil shape, thereby further causing the wire to cut through the layers of tissue and create a shunt of a diameter less than the diameter of the outer loops such that the at least two outer loops do not pass through said shunt.

Optionally, at least one end of the wire comprises a connection means for connecting with a delivery device. The connection means may comprise a nut and a screw.

Optionally, a diameter of the wire when in a coil shape ranges between 0.1 mm to 10 mm and a length of the wire ranges from 1 cm to 250 cm.

Optionally, the wire comprises Nitinol.

Optionally, the plurality of magnets are positioned on the at least two inner loops such that repulsive forces between adjacent magnets of the plurality of magnets on a same one of the at least two inner loops cause said adjacent magnets to maintain a predefined distance between them.

Optionally, the plurality of magnets are rare earth magnets covered with at least one of gold, nickel or titanium.

Optionally, the wire, when in a coiled shape, has a maximum cross sectional diameter ranging from 5 mm to 50 mm.

Optionally, each of the plurality of magnets has a maximum cross sectional length ranging from 0.2 mm to 7 mm and a pull force ranging from 0.1 lb. to 4 lb.

Optionally, a pull force between any two consecutively placed magnets of the plurality of magnets is approximately 2.318 N.

Optionally, a length, an inner diameter and an outer diameter of each of the plurality of magnets is 3 mm, 0.66 mm and 2.5 mm respectively.

A shape of the shunt formed by using the shunt device may be determined by a shape of the at least two inner loops.

Optionally, at least 50% of the adjacent magnets on each loop are arranged with like poles facing each other.

Optionally, adjacent magnets on each of the at least two inner loops are separated by a non-ferromagnetic spacer, thereby preventing adjacent magnets from attaching to each other.

Optionally, each of the at least two outer loops are connected to opposing ends of the at least two inner loops.

Optionally, two opposing tips of the wire correspond to ends of the at least two outer loops and comprise a crimped probe at one of the two opposing tips and a cautery probe at a second of the two opposing tips. The crimped probe may be attached to a screw as a connection means for connecting the wire with a delivery device. A magnet of the plurality of magnets may at least partially encompass the cautery probe or the screw. The delivery device may comprise a mechanism for heating the shunt device prior to deploying in the body of the patient.

Optionally, each of the at least two outer loops is wave-shaped so that a location of each crest of one of the at least two outer loops is aligned with each trough of a second of the at least two outer loops.

Optionally, the shunt device further comprises a heat source adapted to be connected to an end of the wire, wherein the heat source is adapted to deliver energy to heat the wire and cause the wire to transform from the substantially straight wire to the coil shape.

The present specification also discloses a method for treating a valve defect in a heart chamber of a patient's body, the method comprising: using a needle positioned in a catheter, piercing a portion of the heart chamber; delivering a wire proximate said portion of the heart chamber, wherein: the wire comprises a shape memory alloy; the wire is adapted to transform from a substantially straight wire to a coil shape upon heating; the wire, upon transforming to the coil shape, comprises at least two inner loops and at least two outer loops; a diameter of at least one of the at least two inner loops is less than a diameter of at least one of the at least two outer loops; the wire, when in the coil shape, is adapted to exert a compressive force upon layers of tissue caught between the at least two inner loops; and a plurality of magnets coupled to the at least two inner loops, wherein the plurality of magnets are adapted to provide a compressive force to adjacent inner loops of the wire in the coil shape.

Optionally, the method further comprises delivering heat to the wire to transform the substantially straight wire to the coil shape using a heat source adapted to be connected to an end of the wire.

The present specification also discloses a method for treating a valve defect in a patient's body, the method comprising: delivering a device into the patient's body, wherein the device comprises a wire made of a shape memory alloy, wherein the wire has a first part, comprising a first end, and a second part, comprising a second end, wherein a first magnet is attached to the first part and wherein a second magnet is attached to the second part; using the first end, piercing a first leaflet of the valve in order to create contact between the first magnet and the first leaflet; and using the first end, piercing a second leaflet of the valve in order to create contact between the second magnet and the second leaflet, the attractive forces between the first and the second magnets causing improved closure of the valve for preventing or reducing back flow through the valve.

Optionally, the method further comprises delivering heat to the wire to transform the substantially straight wire to the coil shape using a heat source adapted to be connected to an end of the wire.

The present specification also discloses a shunt device for treating a valve defect in a patient's body, the device comprising: a first magnet coupled with a first shape memory alloy (SMA) wire adapted to change shape from a predominantly linear wire into a coil when deployed within the body; and a second magnet coupled with a second shape memory alloy (SMA) wire adapted to change shape from a predominantly linear wire into a coil when deployed within the body; the first wire piercing a first leaflet of the valve for attaching the first magnet with the first leaflet, the second wire piercing a second leaflet of the valve for attaching the second magnet with the second leaflet, the attractive forces between the first and the second magnets causing improved closure of the valve for preventing or reducing back flow through the valve.

Optionally, the shunt device further comprises means of coupling with a delivery device for deploying the device for treating a valve defect at a predefined site within a body, the delivery device comprising: a delivery catheter for pushing the device in through an insertion tube of a catheter and out at the site through a tip of an catheter, wherein the delivery catheter comprises a threaded distal end for coupling with the device for treating a valve defect and wherein the catheter is adapted to be rotated to release said device at the deployment site. Optionally, the delivery device further comprises a non-cautery needle adapted to pierce a tissue for deploying the device for treating a valve defect therein. Optionally, the delivery device further comprises a mechanism for heating the first and the second SMA wires prior to deploying in the patient's body.

The present specification also discloses shunt devices for creating a shunt in an atrial septum, comprising a plurality of magnets coupled to at least two inner loops of a coil comprising at least two inner loops and two outer loops, a diameter of each of the inner loops being less than a diameter of the outer loops, said coil being comprised of a shape memory alloy (SMA), wherein the coil is adapted to exert a compressive force upon layers of tissue caught between the inner loops of the coil, and wherein the plurality of magnets are adapted to provide a compressive force to adjacent inner loops of the coil, thereby further causing the coil to cut through the layers of tissue and create a shunt of a diameter less than the diameter of the outer loops, thereby preventing the outer two loops from passing through the created shunt, wherein at least one end of the coil comprises a connection means for connecting with a delivery device.

The connection means may be one of a nut and a screw.

Optionally, a diameter of the coil ranges between 0.1 mm to 10 mm and a length of the coil ranges from 1 cm to 250 cm.

The SMA coil may be a Nitinol coil.

Optionally, the magnets are positioned such that repulsive forces between adjacent magnets on the same coil cause said adjacent magnets to maintain a predefined distance between said adjacent magnets.

Optionally, the magnets are rare earth magnets covered with at least one of gold, nickel and titanium.

Optionally, when in a coiled state, a maximum cross sectional diameter of the SMA coil ranges from 5 mm to 50 mm.

Each of the magnets may have a maximum cross sectional length ranging from 0.2 mm to 7 mm and a pull force ranging from 0.1 lb. to 4 lb.

Optionally, a pull force between any two of the consecutively placed magnets on the coil is approximately 2.318 N.

Optionally, a length, inner diameter and outer diameter of each of the magnets is 3 mm, 0.66 mm and 2.5 mm respectively.

A shape of the shunt formed by using the SMA coil and magnets may be determined by the shape of the coiled SMA coil.

Optionally, at least 50% of the adjacent magnets on each loop of the coil are arranged with like poles facing each other, thereby creating a repulsive force between two adjacent magnets in a single inner loop of the coil.

Optionally, two adjacent magnets on a single inner loop of the coil are separated by a non-ferromagnetic spacer, thereby preventing the two adjacent magnets from attaching to each other.

The present specification also discloses a delivery device for deploying a cardiac shunt device at a predefined site within a body, the shunt device comprising a plurality of magnets coupled to at least two inner loops of a coil comprising at least two inner loops and two outer loops, a diameter of each of the inner loops being less than a diameter of the outer loops, the delivery device comprising: a delivery catheter for pushing the device in through an insertion tube of a catheter and out at the site through a tip of an catheter, wherein the delivery catheter comprises a threaded distal end for coupling with the shunt device and wherein the catheter is adapted to be rotated to release the shunt device at the deployment site.

Optionally, the delivery device further comprises a non-cautery needle adapted to pierce a tissue for deploying the shunt device therein.

Optionally, the delivery device further comprises a mechanism for heating the SMA coil prior to deploying the shunt device, therein assisting in shape transformation of the device from a pre-deployment configuration to a post-deployment configuration.

The present specification also discloses a device for treating a valve defect comprising a first magnet coupled with a first shape memory alloy (SMA) wire adapted to change shape from a non-coiled wire into a coil when deployed within a body, and a second magnet coupled with a second shape memory alloy (SMA) wire adapted to change shape from a non-coiled wire into a coil when deployed within a body, the first wire piercing a first leaflet of a valve for attaching the first magnet with the leaflet, the second wire piercing a second leaflet of the valve for attaching the second magnet with the second leaflet, the attractive forces between the first and the second magnets aiding complete closure of the valve and preventing or restricting back flow. While during forward flow, the pressure from flow on the leaflets separates the magnets and, as the distance between magnets increases, the attraction force decreases. Therefore, the valve defect device does not produce any significant impairment of valvular function during forward flow.

The present specification also discloses a delivery device for deploying a device for treating a valve defect at a predefined site within a body, the delivery device comprising: a delivery catheter for pushing the device in through an insertion tube of a catheter and out at the site through a tip of the catheter, wherein the delivery catheter comprises a threaded distal end for coupling with the device for treating a valve defect and wherein the catheter is adapted to be rotated to release said device at the deployment site.

Optionally, the delivery device further comprises a non-cautery needle adapted to pierce a tissue for deploying the valve defect device therein.

Optionally, the SMA wires in the device is adapted to make the puncture.

Optionally, the delivery device further comprises a mechanism for heating the SMA coil prior to deploying the valve defect device, therein assisting in shape transformation of the device from a pre-deployment configuration to a post-deployment configuration.

The aforementioned and other embodiments of the present shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 7 is a flowchart illustrating the steps of using a coiled SMA wire for creating a septal defect in a human heart, in accordance with an embodiment of the present specification;

FIG. 8A illustrates a human heart comprising a mitral valve;

FIG. 8B illustrates a human heart suffering from a mitral valve prolapse condition;

FIG. 10A illustrates a magnet being delivered to a mitral valve leaflet, in accordance with an embodiment of the present specification;

FIG. 10B illustrates leaflets of the mitral valve closed due to attraction between the magnets, in accordance with an embodiment of the present specification;

FIG. 10C illustrates an SMA wire coupled with a magnet, in accordance with an embodiment of the present specification;

FIG. 10D illustrates a non-linear configuration of a SMA wire, upon being delivered at a deployment site, in accordance with an embodiment of the present specification;

FIG. 10E illustrates another non-linear configuration of a SMA wire, upon being delivered at a deployment site, in accordance with an embodiment of the present specification;

FIG. 10F illustrates another non-linear configuration of a SMA wire, upon being delivered at a deployment site, in accordance with an embodiment of the present specification;

FIG. 11A illustrates a plurality of heart valves closed by using magnets threaded in SMA wires, in accordance with an embodiment of the present specification;

FIG. 11B illustrates a magnet threaded in an SMA wire deployed at a valve site, in accordance with an embodiment of the present specification;

FIG. 14A illustrates a side view of a device for creating a septal defect and comprising an SMA wire with a plurality of magnets, in accordance with an embodiment of the present specification;

FIG. 14B illustrates a cross sectional view of the device for creating a septal defect of FIG. 14A;

FIG. 14C illustrates a top-down view of the device for creating a septal defect of FIG. 14A;

FIG. 14D illustrates a perspective view of the device for creating a septal defect of FIG. 14A;

FIG. 15A illustrates a side view of a device for creating a septal defect and comprising two SMA wires with a plurality of magnets, in accordance with an embodiment of the present specification;

FIG. 15B illustrates a cross sectional view of the device for creating a septal defect of FIG. 15A;

FIG. 15C illustrates a top-down view of the device for creating a septal defect of FIG. 15A;

FIG. 15D illustrates a perspective view of the device for creating a septal defect of FIG. 15A;

DETAILED DESCRIPTION

Figure 1:
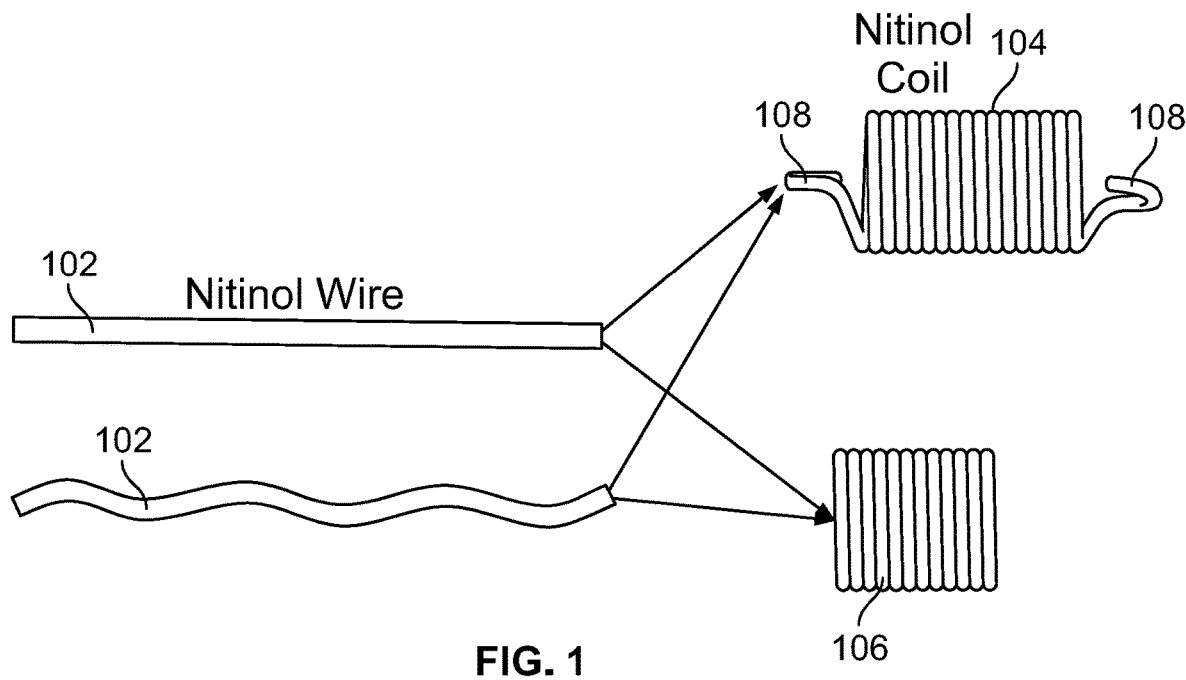
FIG. 1 illustrates a straight shape memory alloy (SMA) wire which coils within a human body, in accordance with an embodiment of the present specification.

In various embodiments, a shape memory alloy (SMA) or smart alloy wire is used to create a shunt. A desired shape and size of the shunt is created by cutting through tissue layers in a human body to create the opening for the shunt. In an embodiment, a straight piece of an SMA wire, or a longitudinally stretched coil, or any other substantially planar structure, is delivered at a location requiring a shunt within a body. In an embodiment, the SMA wire is either superelastic or heat sensitive and curls up into a spring like coil in response to body heat within the body. In various embodiments, the wire has a straight or a longitudinally stretched coil or an elongate shape at room temperature and a compressed coil shape at the human body temperature, which is in the preferred range of 97.7 degrees Fahrenheit (F) to 99.5 degrees F. The coil may take a compressed shape at any temperature greater than 96 degrees F.

In another embodiment, a coiled Nitinol wire having at least two inner loops and at least two outer loops, wherein the diameter of the inner loops is less than the diameter of the outer loops, is used to create a septal defect or shunt between two chambers of a human heart. The inner loops of the wire are threaded with magnets to increase the compressive force between the coil loops creating the shunt, while the outer loops are used to anchor the coil in a desired position and prevent dislodgement at any time during or after the shunt formation.

The compressed coil defines the desired shape and dimensions of the desired shunt. The compressing coil produces a compression force on tissue caught between loops of the coil. The coiling action also causes the wire to create ischemia, pressure necrosis and cut through the desired tissue layers, creating a shunt between two adjacent body tissues. In an embodiment, a plurality of magnets is provided on at least two loops of the coiled wire. Magnets provided on adjacent rings attract each other, thereby enhancing the cutting action of the coil. In some embodiments, compression force is provided by the combination of the coiling wire and attraction force between the magnets. In some embodiments, the shape of the resultant shunt is predominantly determined by the shape of the coil and not by the forces between the magnets. In various embodiments, the number of magnets used and the length of the magnets are determined by the shape, dimensions or time needed to form a shunt.

The term "and/or" means one or all of the listed elements or a combination of any two or more of the listed elements.

The terms "comprises" and variations thereof do not have a limiting meaning where these terms appear in the description and claims. In the description and claims of the application, each of the words "comprise" "include" and "have", and forms thereof, are not necessarily limited to members in a list with which the words may be associated.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

FIG. 1 illustrates a straight SMA wire 102 which coils up within a human body, in accordance with an embodiment of the present specification. Wire 102 is made of an SMA material such as Nitinol (NiTi). A shape-memory alloy (SMA, smart metal, memory metal, memory alloy, muscle wire, smart alloy) is an alloy that "remembers" its original shape and that when deformed returns to its pre-deformed shape when heated. NiTi alloys change from martensite to austenite upon heating. In an embodiment, the SMA wire 102 is made of a copper-aluminum-nickel alloy. In another embodiment the SMA wire 102 is made of a nickel-titanium alloy. In an embodiment, a diameter of the wire 102 ranges between 0.1 to 6 mm and the wire 102 has a maximum strain of less than 10% in an uncoiled position and a maximum cross sectional dimension ranging from 5 mm to 50 mm. In various embodiments, for a 5% strain, and for wire diameters less than 0.75 mm, ranging between 0.75 mm and 1 mm, and greater than 1 mm, the diameters of the coiled up wires are less than 15 mm, between 15 mm and 20 mm, and greater than 20 mm respectively. In an embodiment, for a 10% strain, and for wire diameters of 1 mm, 1.25 mm, 1.5 mm, 1.7 mm, 2 mm and 2.5 mm, the diameters of the coiled up wires are 10 mm, 12.5 mm, 15 mm, 17 mm, 20 mm and 25 mm respectively. In an embodiment, for a 6% strain, and for wire diameters of 0.6 mm, 0.75 mm, 0.9 mm, 1.02 mm, 1.2 mm and 1.5 mm, the diameters of the coiled up wires are 5 mm, 10 mm, 12.5 mm, 15 mm, 17 mm, 20 mm and 25 mm respectively. Further, in various embodiments, the wire 102 coils up into at least 2 loops upon delivery into a body.

$A_s$ and $A_f$ are the temperatures at which the transformation from martensite to austenite starts and finishes. Upon insertion into a human body and placement at a shunt site, wire 102, depicting a pre-deployment configuration, changes shape and coils up as coil 104 or 106, depicting a post-deployment configuration, in response to the higher temperature of the human body relative to the room temperature. In embodiments, wire 102 changes shape and coils up as 104 or 106 in response to an input of energy, such as electrical energy generating internal resistance and heat, into one end of the wire. It should be appreciated that wherever heat from the body is mentioned herein, such heat may be augmented by the application of energy, such as electrical energy, to increase the amount of heat in the wire and to improve the transition to austenite. Such an application may occur by attaching the wire, at one end, to a detachable second wire, wherein the second wire is adapted to receive, and transmit, electrical or heat energy. In some embodiments, connecting components 108 are provided at one or more ends of the wire 102 for attachment with a delivery catheter. In an embodiment, the delivery catheter comprises a mechanism for heating the SMA wire 102 during deployment for assisting in shape transformation of the wire from the pre-deployment configuration to the post-deployment configuration. In various embodiments, the $A_f$ temperature of the wire is less than or equal to 40° C. and $A_s$ temperature of the wire is less than or equal to 37° C. In various embodiments, the strain on the Nitinol wire in its martensite shape is less than or equal to 10%. In one embodiment, the coil has a circular cross-section with a radius r where the circumference of the coil is $2\pi r$ and the area of the coil is $\pi r^2$ wherein the coil creates a shunt opening of a radius approximately r and area $\pi r^2$. In various embodiments, the diameter of the wire 102 ranges from 0.1 mm to 10 mm and the length of the wire 102 ranges from 1 cm to 250 cm.

Figure 2:
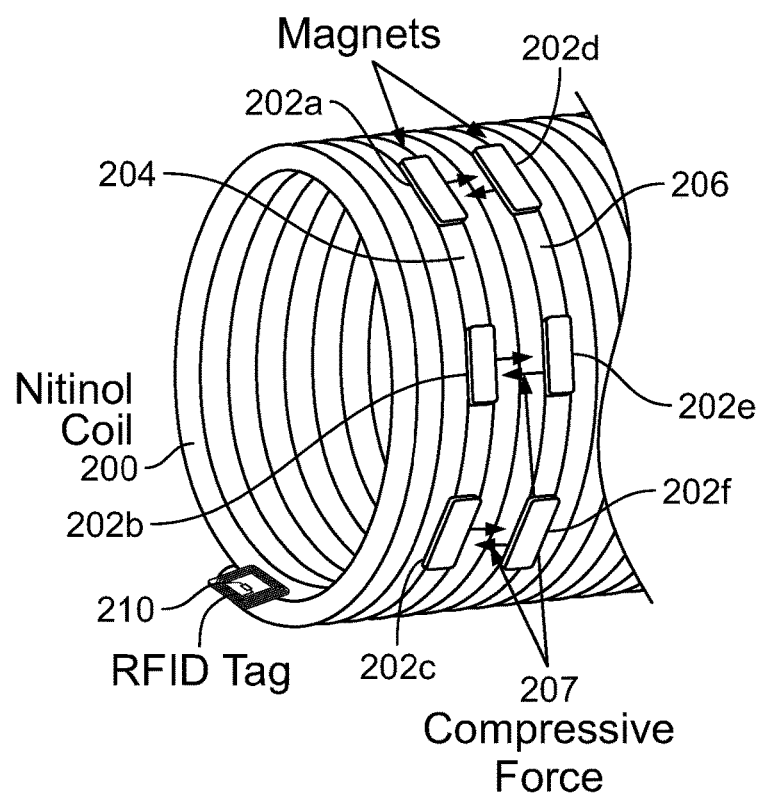
FIG. 2 illustrates a plurality of magnets threaded on loops of an SMA wire, in accordance with an embodiment of the present specification.

FIG. 2 illustrates a plurality of magnets 202a, 202b, 202c, 202d, 202e, 202f threaded on loops 204, 206 of an SMA wire, in accordance with an embodiment of the present specification. Magnets 202a, 202b, 202c, 202d, 202e, 202f are threaded on loops 204 and 206 of coil 200. In an embodiment, coil 200 is a Nitinol wire that coils up in response to temperature change. A repulsive force acts between adjacent magnets 202a, 202b and 202c which are threaded on the same loop 204, thereby maintaining a desired distance between said magnets. Similarly, a repulsive force acts between adjacent magnets 202d, 202e and 202f which are threaded on the same loop 206, thereby maintaining a desired distance between these magnets. An attractive force acts between the magnets threaded on loop 204 and the magnets on loop 206. Hence, there is attraction between the magnets 202a and 202d, between magnets 202b and 202e, and between magnets 202c and 202f. The attraction between the magnets on adjacent loops creates a compressive force 207 between loops of the coil, drawing the loops together to cut tissue between the loops and allow for shunt formation. In an embodiment, at least two magnets are coupled with two adjacent loops of the coil 200 and the wire coils up into at least two loops. In an embodiment, the magnets are rare earth magnets covered with a biocompatible material such as gold, nickel, Teflon, parylene, copper, zinc, silicone, epoxy or titanium. In an embodiment, the coil 200 includes an RFID tag 210 to assist in the localization of the coil 200 after deployment and during shunt formation. Using an RFID scanner, the position of the coil can be identified, through communications with the embedded RFID tag, to determine the precise location of the coil in the patient without the need for radiation for visualization.

In one embodiment, the Nitinol coil applies an amount of pressure less than or equal to 50 mm Hg on the tissue and the combined coil and magnets apply an amount of pressure greater than 50 mm Hg on the tissue. In another embodiment, the Nitinol coil applies an amount of pressure less than or equal to 80 mm Hg on the tissue and the combined coil and magnets apply an amount of pressure greater than 80 mm Hg on the tissue. In yet another embodiment, the Nitinol coil applies an amount of pressure less than or equal to 120 mm Hg on the tissue and the combined coil and magnets apply an amount of pressure greater than 120 mm Hg on the tissue. In yet another embodiment, the Nitinol coil applies an amount of pressure less than or equal to 150 mm Hg on the tissue and the combined coil and magnets apply an amount of pressure greater than 150 mm Hg on the tissue. In another embodiment, the Nitinol coil applies an amount of pressure less than or equal to 200 mm Hg on the tissue and the combined coil and magnets apply an amount of pressure greater than 200 mm Hg on the tissue. In an embodiment, the coil pressure at each coil tissue interface is sufficient to impede the capillary flow in the tissue by greater than 50%. In an embodiment, the coil creates a pressure of more than or equal to 20 mm Hg at more than one fourth of the circumference of coil and the pressure is relatively equally distributed among the two semicircles of each coil loop. In an embodiment, the pressure is more than or equal to 20 mm Hg at two or more points that are on the opposite sides on each coil loop.

In some embodiments, the shunt device is connected to a delivery device by a nut and a screw. In other embodiments, the shunt device is connected to a delivery device by a grasping mechanism. In embodiments, a diameter of the coil ranges between 0.1 mm to 10 mm and a length of the coil ranges from 1 cm to 250 cm. In various embodiments, when in a coiled state, a maximum cross sectional diameter of the SMA coil ranges from 5 mm to 50 mm. In embodiments, each of the magnets has a maximum cross sectional length ranging from 0.2 mm to 7 mm and a pull force ranging from 0.1 lb. to 4 lb. In embodiments, a pull force between any two of the consecutively placed magnets on the coil is approximately 2.318 N. In some embodiments, a length, inner diameter and outer diameter of each of the magnets is 3 mm, 0.66 mm and 2.5 mm respectively. In embodiments, a shape of the shunt formed by using the SMA coil and magnets is determined by the shape of the coiled SMA coil. In some embodiments, at least 50% of the adjacent magnets on each loop of the coil are arranged with like poles facing each other, thereby creating a repulsive force between two adjacent magnets in a single inner loop of the coil.

In some embodiments, the majority of the compressive force, as described above, is initially provided by the SMA coil. However, as the magnets physically converge closer together, the magnetic compressive force overtakes the compressive force provided by the Nitinol coil and drives the shunt formation.

Figure 3A:
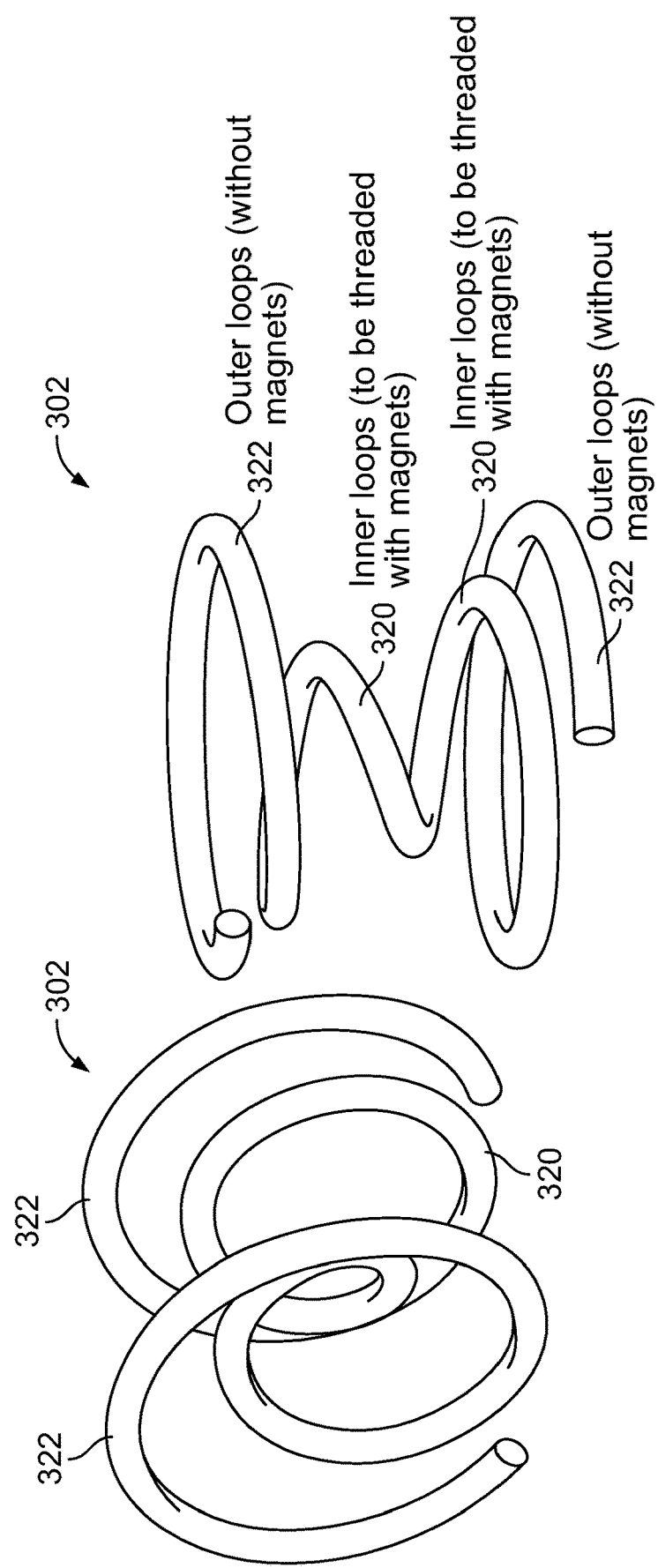
FIG. 3A illustrates a coiled shunt wire, in accordance with an embodiment of the present specification.
Figure 3B:
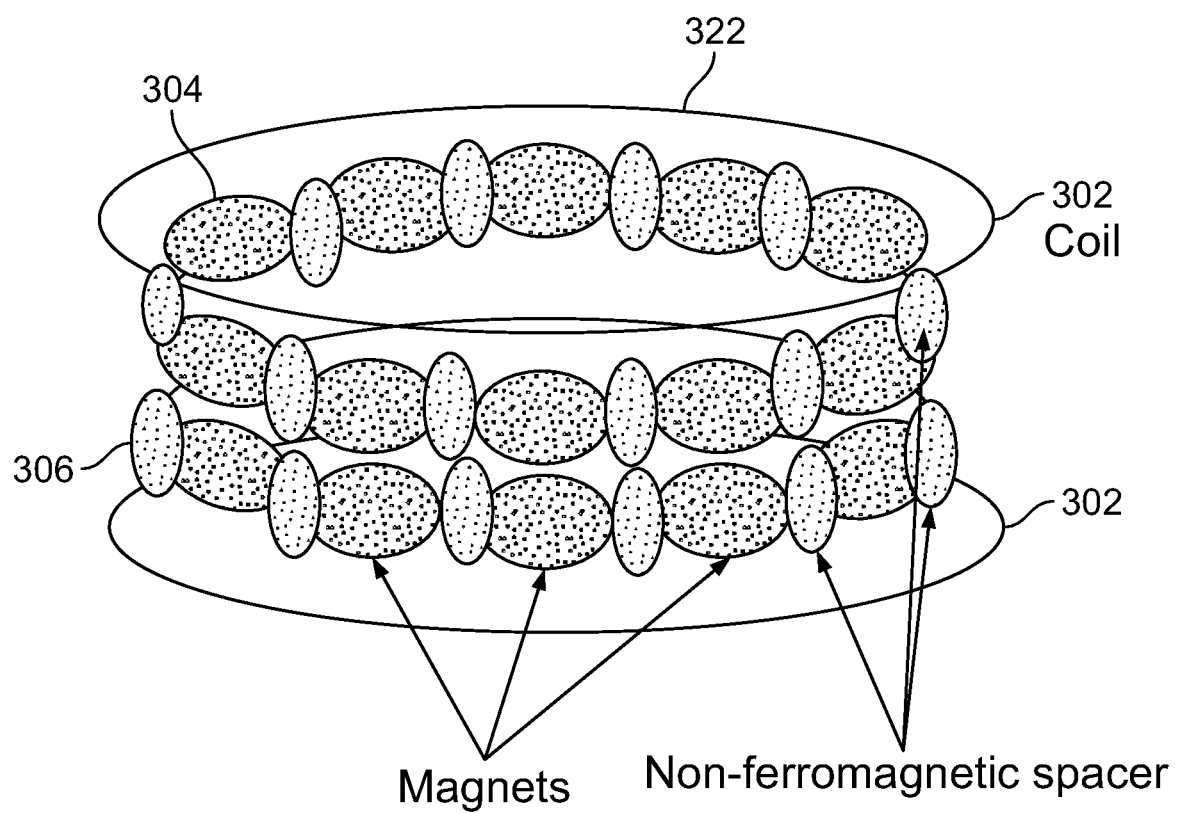
FIG. 3B illustrates a plurality of magnets and spacers threaded on inner loops of the coiled shunt wire shown in FIG. 3A.
Figure 3C:
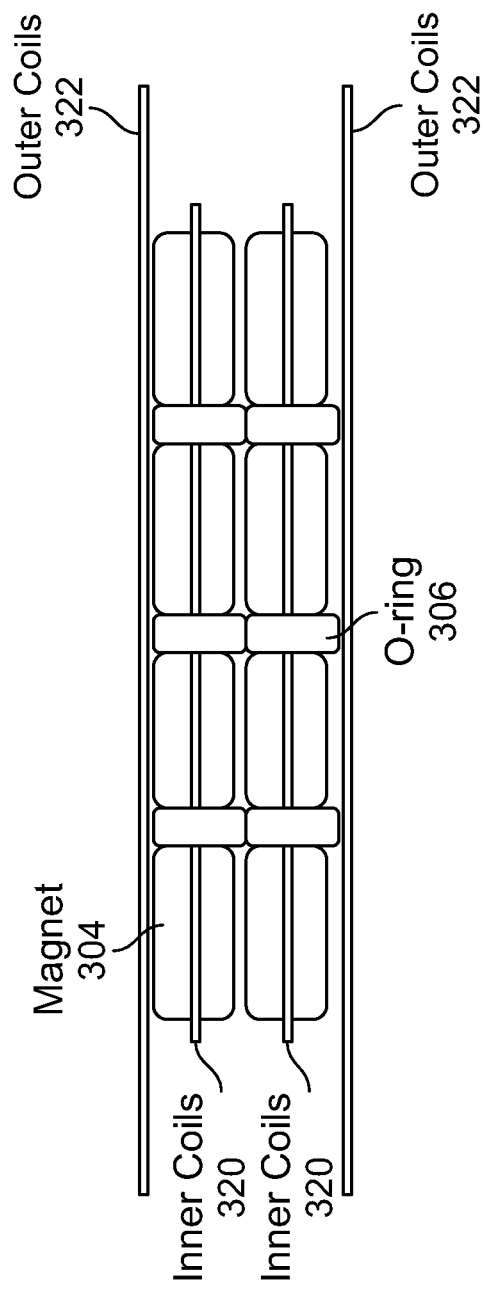
FIG. 3C illustrates a diagrammatic view of a plurality of magnets and spacers threaded on inner loops of the coiled shunt wire shown in FIG. 3A.

FIG. 3A illustrates a coiled shunt wire, in accordance with an embodiment of the present specification. Coil 302 comprises two inner loops 320 and two outer loops 322, wherein a diameter of the inner loops 320 is less than a diameter of the outer loops 322 of coil 302. FIG. 3B illustrates a plurality of magnets 304 and spacers 306 threaded on inner loops 320 of the coiled shunt wire shown in FIG. 3A. FIG. 3C illustrates a diagrammatic view of a plurality of magnets 304 and spacers 306 threaded on inner loops 320 of the coiled shunt wire shown in FIG. 3A. Referring to FIGS. 3A, 3B and 3C, the inner loops 320 of coil 302 are threaded with two or more rows of magnets 304 and spacers 306, while two or more outer loops 322 of coil 302 do not have magnets and spacers threaded on them. The diameter of the inner loops 320 is less than the diameter of the outer loops 322 of coil 302. The compressive force of the magnets 304 creates a septal defect or shunt of a diameter less than the diameter of the outer loops 322, thereby preventing the outer two loops 322 from passing through the septal defect, anchoring the coil 302 to the septal defect and hence preventing its spontaneous passage after a septal defect is formed.

In embodiments, spacers 306 are included on the coil 302 between each pair of magnets 304 for decreasing the number of magnets required for achieving a required compressive force. In an embodiment, the spacers 306 are composed of a non-ferromagnetic or biocompatible material. In various embodiments, the spacers 306 comprise silicone or Nitinol tubes or O-rings or circular balls. In an embodiment, an outer diameter of a spacer 306 ranges between 25% and 300% of the outer diameter of a magnet 304 and a length of a spacer 306 is less than five times a length of a magnet 304.

Figure 4:
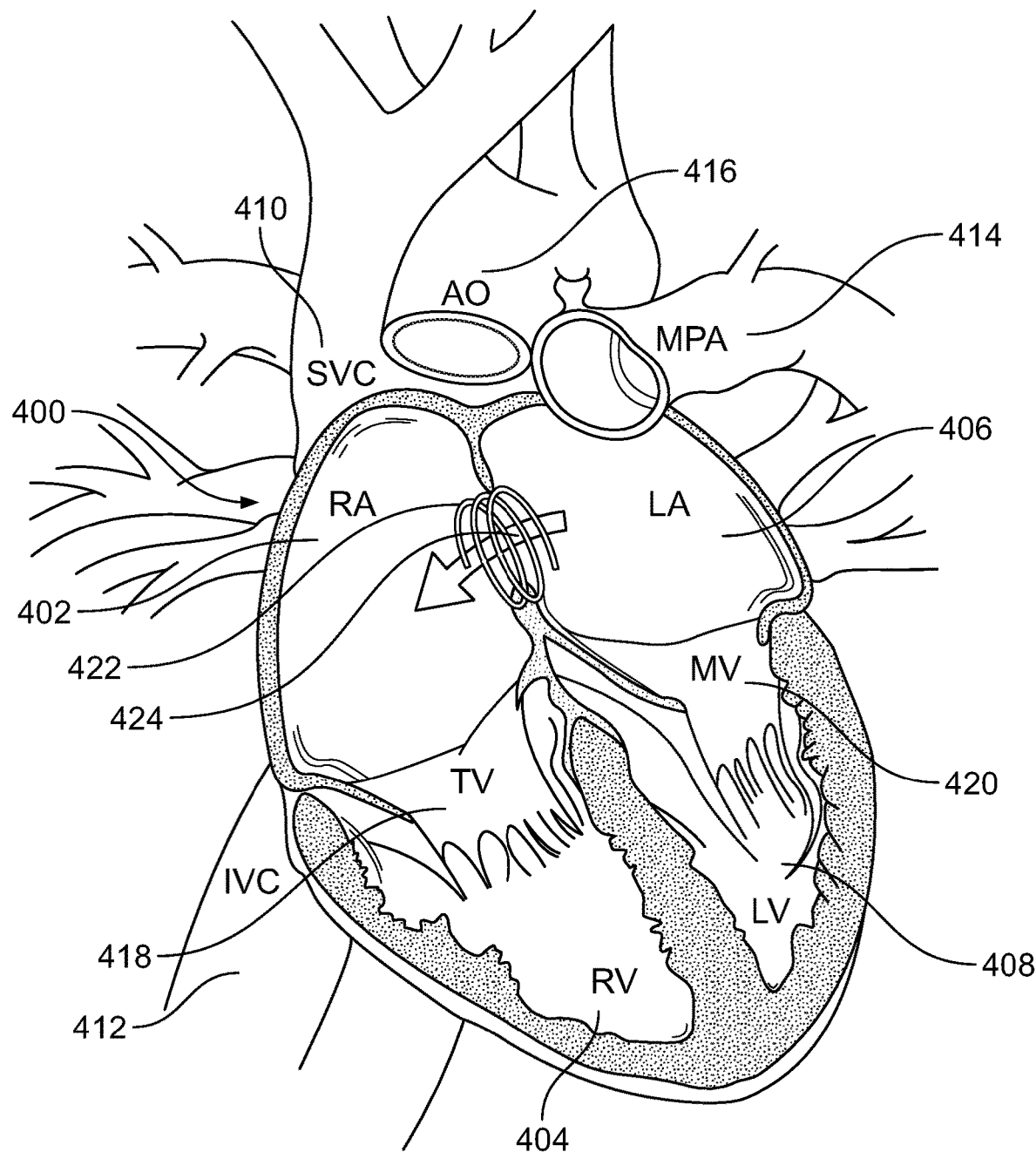
FIG. 4 illustrates a human heart with a coiled SMA wire creating a septum defect, in accordance with an embodiment of the present specification.

FIG. 4 illustrates a human heart 400 with a coiled SMA wire 422 creating a septal defect 424, in accordance with an embodiment of the present specification. Heart 400 comprises a right atrium 402, a right ventricle 404, a left atrium 406, a left ventricle 408, a tricuspid valve 418, and a mitral valve 420. Also depicted in relation to the heart 400 are a superior vena cava 410, an inferior vena cava 412, a main pulmonary artery 414, and an aorta 416. In cases of heart disease, such as one which requires decompression of one of the chambers of the heart (e.g. the left atrium 406), a septal defect or shunt 424 is created by using a coiled SMA wire 422. The SMA coil 422, which, in an embodiment, comprises a Nitinol wire, is delivered through a hole punctured by a catheter or needle in the left atrium wall via an endoscope. In other embodiments, the SMA wire 422 in the device is adapted to make the puncture. In response to exposure to body heat, the Nitinol wire changes shape and coils up, holding the tissue of the left atrium 406 wall and the right atrium 402 wall in between the turns of coil 422 as shown in FIG. 4, thereby forming a shunt 424 between the left atrium 406 and the right atrium 402 and decompressing the left atrium 406. In some embodiments, the device comprises a heat source adapted to be connected to an end of the wire, wherein the heat source is adapted to deliver energy to heat the wire and cause the wire to transform from the substantially straight wire to the coil shape. In an embodiment, magnets may be threaded on the coil 422 (such as shown in FIGS. 3B and 3C) to further increase the compressive force. In various embodiments, the shunt is formed over a period of time, allowing for neovascularization of the shunt to occur, resulting in a robust and stable shunt. Creating the shunt over a period of time allows pressure in a high-pressure system (pressure is high in the left atrium) to be relieved more slowly than in prior art approaches. Slowly relieving the pressure lessens the burden placed on the right heart, thereby reducing the risk of sudden cardiac failure during shunt creation.

Figure 5A:
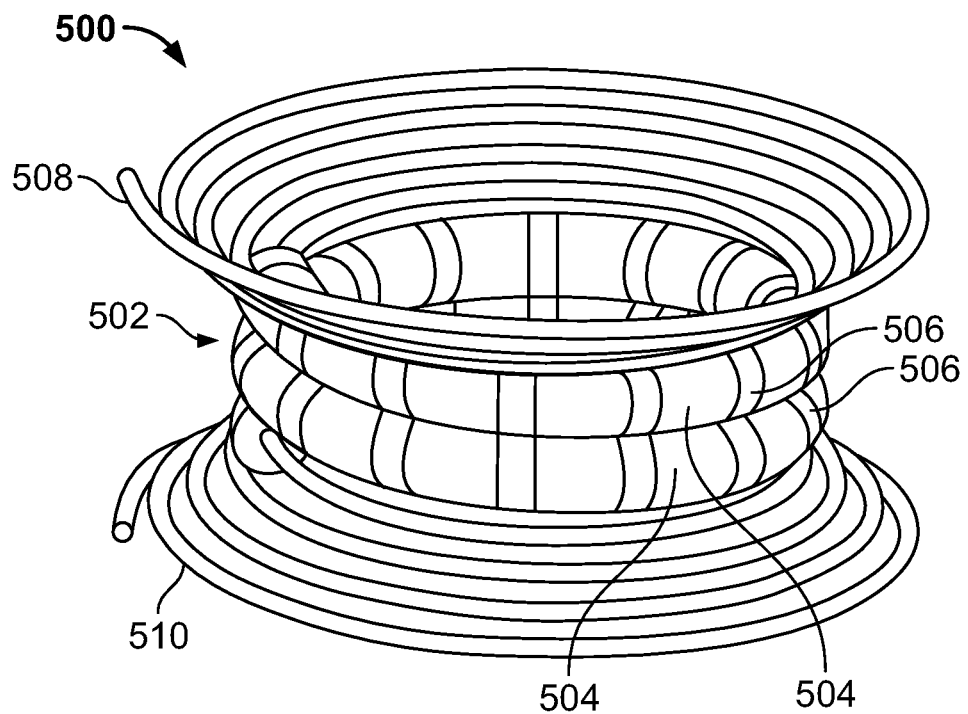
FIG. 5A illustrates a diagrammatical representation of an SMA coil for creating a septal defect, in accordance with an embodiment of the present specification.
Figure 5B:
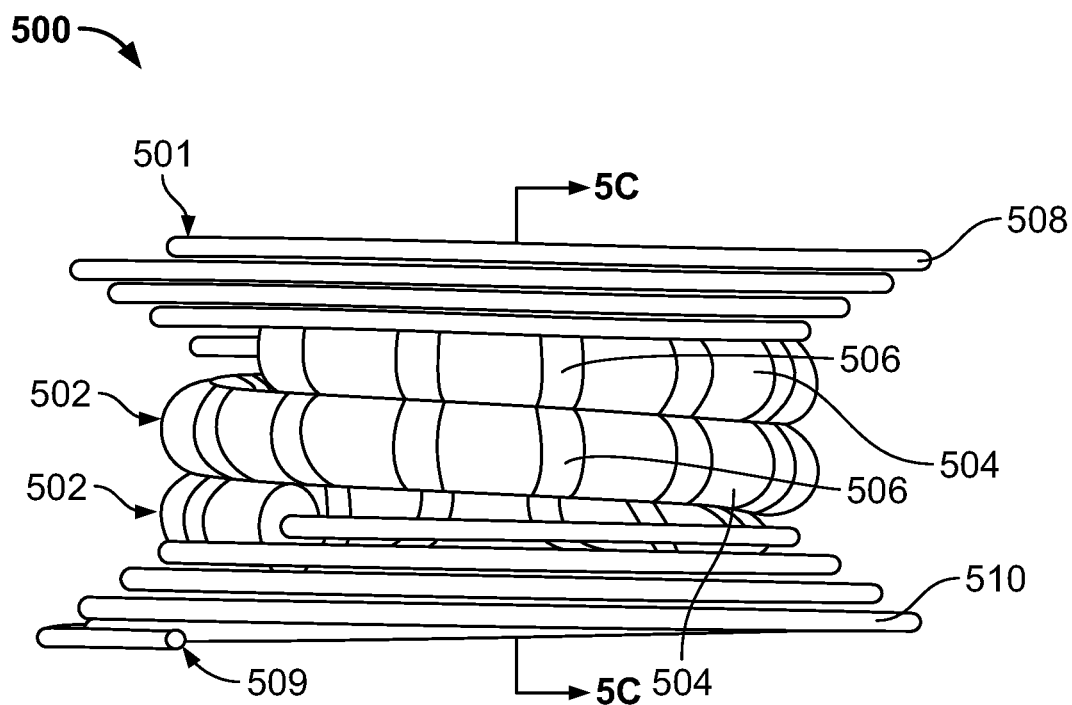
FIG. 5B is another view of the SMA coil for creating a septal defect shown in FIG. 5A.
Figure 5C:
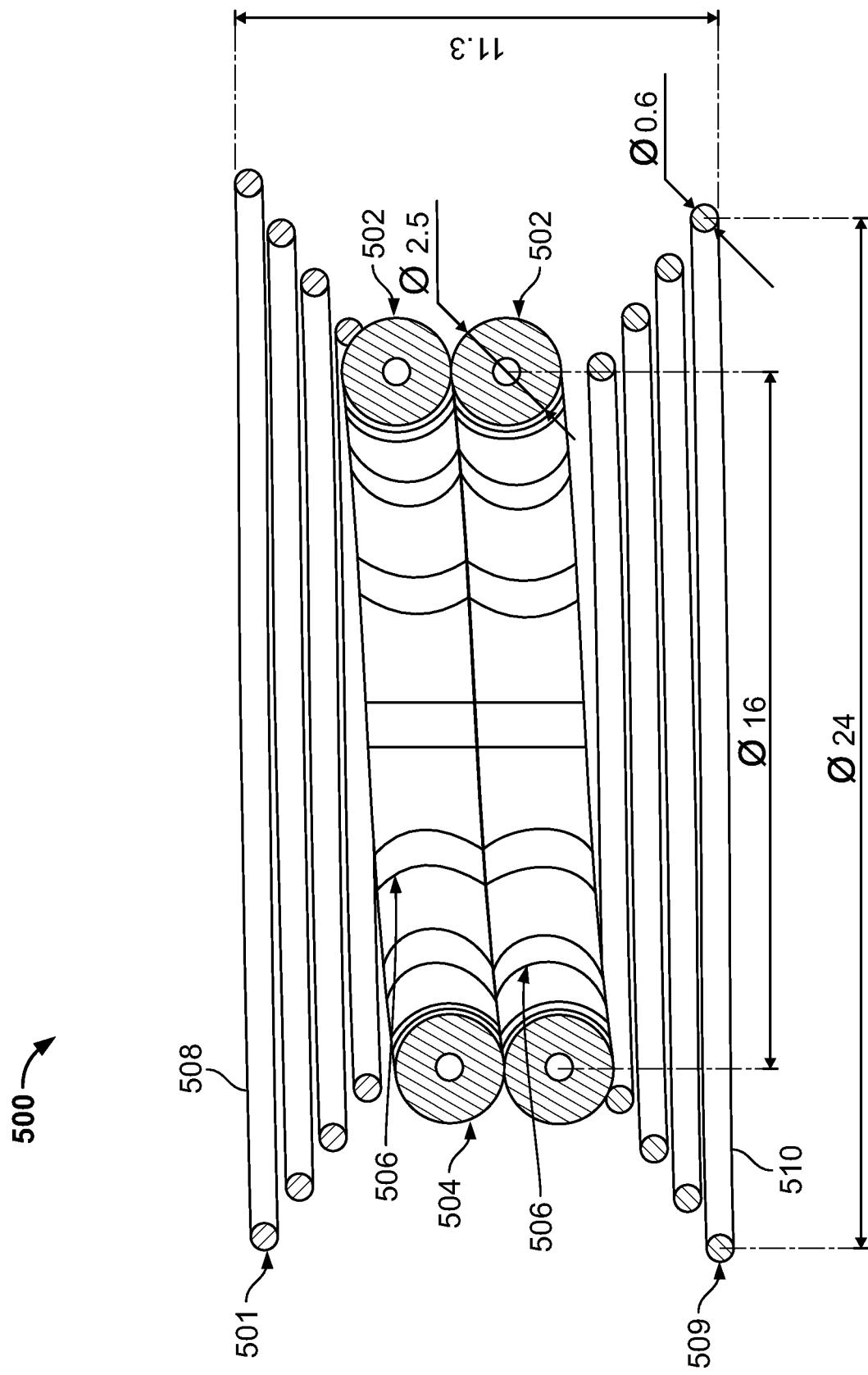
FIG. 5C illustrates a cross sectional view of the SMA coil for creating a septal defect shown in FIG. 5A.

FIG. 5A illustrates a diagrammatical representation of an SMA coil 500 for creating a septal defect, in accordance with an embodiment of the present specification. FIG. 5B is another view of the SMA coil 500 for creating a septal defect shown in FIG. 5A. FIG. 5C illustrates a cross sectional view of the SMA coil 500 for creating a septal defect shown in FIG. 5A. Referring to FIGS. 5A, 5B and 5C simultaneously, coil 500 comprises two inner loops 502 threaded with magnets 504 interspersed with spacers 506 and two outer loops 508 and 510 having diameters larger than diameters of the inner loops 502. In an embodiment, diameters of the inner loops 502 and the outer loops 508, 510 of the coil 500 are approximately 16 mm and 24 mm respectively. In an embodiment, a width of the coil 500, measured from a proximal end 501 to a distal end 509 of the coil 500, is approximately 11.3 mm and a thickness of SMA wire forming the coil 500 is approximately 0.6 mm. In an embodiment, a diameter of the magnets 504 and a diameter of the spacers 506 are approximately 2.5 mm. In various embodiments, the spacers 306 comprise silicone or Nitinol tubes or O-rings or circular balls. One of the outer loops 508 is placed at a proximal end of a wall of a first organ or tissue portion and the other outer loop 510 is placed at a distal end beyond a wall of a second organ or tissue portion.

Figure 6B:
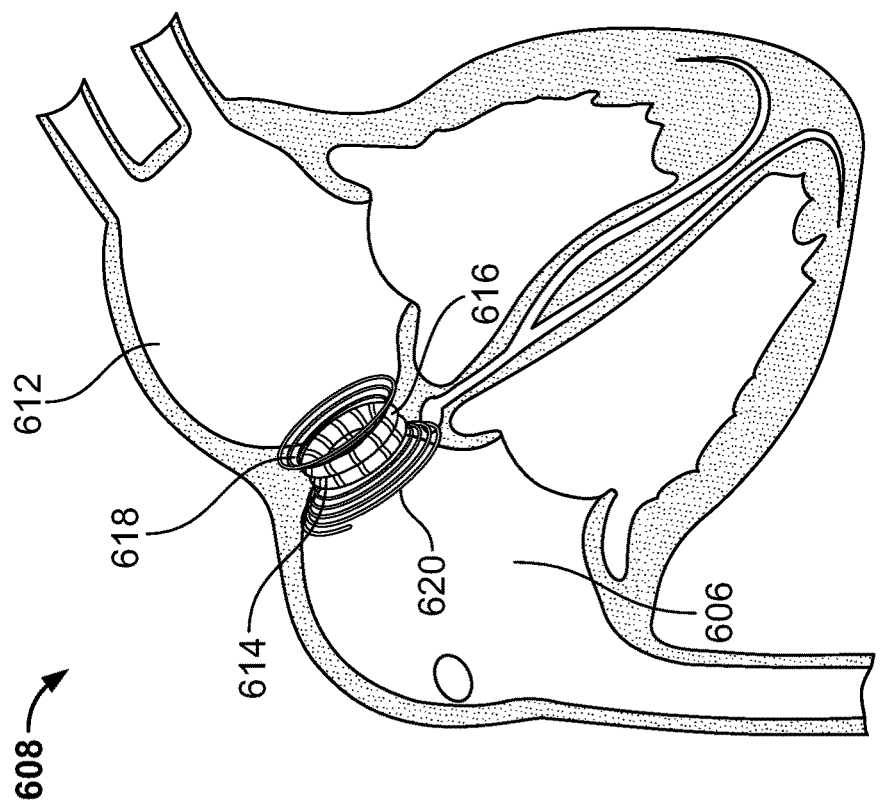
FIG. 6B illustrates an SMA coil comprising magnets deployed within the left and right atriums through the puncture created in the wall for causing a septal defect in the wall, in accordance with an embodiment of the present specification.
Figure 6A:
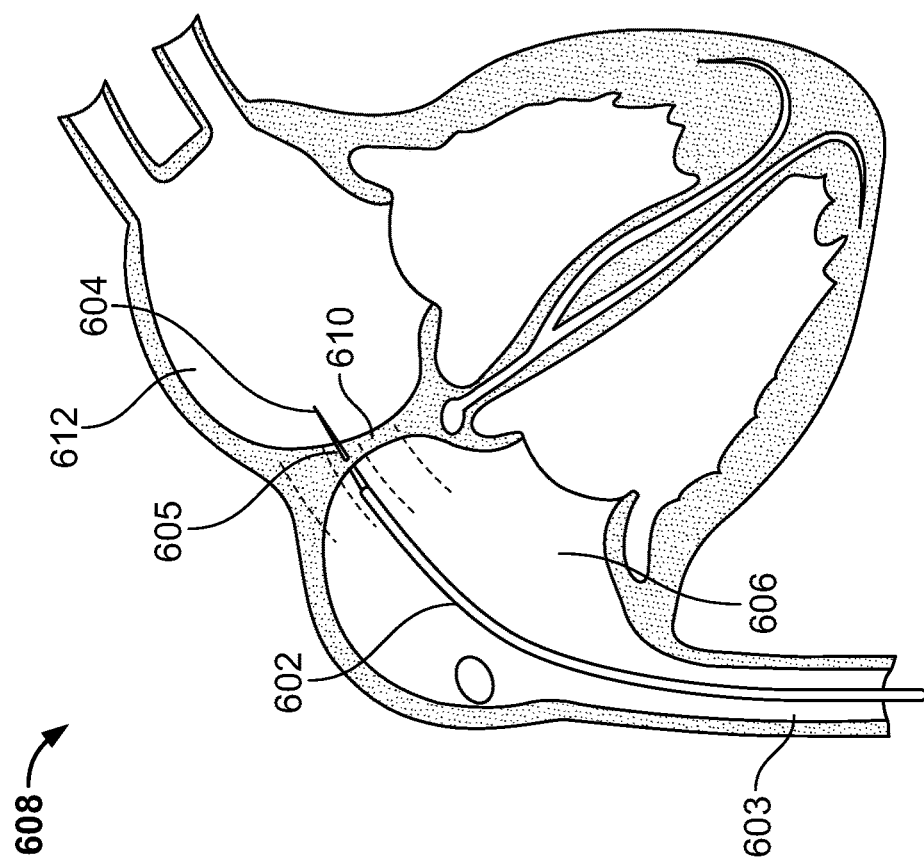
FIG. 6A illustrates a catheter carrying a needle being deployed in a human heart for creating a puncture in a wall between the left and right atriums of the heart, in accordance with an embodiment of the present specification.

FIG. 6A illustrates a catheter 602 carrying a needle 604 being deployed in a human heart 608 for creating a puncture or hole 605 in a wall or atrial septum 610 between the left and right atriums 612, 606 of the heart 608, in accordance with an embodiment of the present specification. FIG. 6B illustrates an SMA coil device 614 comprising magnets deployed within the left and right atriums 612, 606 through the puncture 605 created in the wall 610 for causing a septal defect in the wall 610, in accordance with an embodiment of the present specification. Referring to FIG. 6A, a transseptal catheter 602 carrying a needle 604 is advanced through an inferior vena cava 603 and delivered within a right atrium 606 of a heart 608 via an endoscope (not shown). The needle 604 is used to puncture the wall/atrial septum 610 between the right atrium 606 and the left atrium 612. The needle 604 is then removed and an endoscope or catheter, carrying the SMA coil device 614 in a substantially linear pre-deployment configuration, is advanced through the puncture 605 such that its distal end is positioned in the left atrium 612. Optionally, in other embodiments, the SMA wire in the device 614 is adapted to make the puncture. The device 614 is delivered, in a substantially linear pre-deployment configuration, via the catheter through the puncture 605 in the atrial septum 610. As the device 614 is extended beyond the distal end of the catheter, exposure to body temperature causes the device to begin coiling into its post-deployment coiled configuration. Once the outer loops at the distal end 618 of the device have been deployed, the catheter is retracted to position its distal end in the puncture. The inner loops are then deployed at the puncture 605 position. The endoscope or catheter is then further retracted to position its distal end in the right atrium 606. The remainder of the device 614 is then deployed such that the outer loops at the proximal end deploy within the right atrium 606. As shown in FIG. 6B, SMA coil device 614 comprising magnets 616 threaded on inner loops (as shown in FIGS. 5A, 5B and 5C) has been deployed in the heart 608 via an endoscope or catheter (not shown), with a distal end 618 pushed in to the left atrium 612 via the puncture 605 made in the septum 610. In a fully deployed position, a proximal end 620 of the coil device 614 remains in the right atrium 606 while the distal end 618 is positioned in the left atrium 612. The inner loops of coil device 614 hold the tissue of the septum 610 between them and the attraction between the magnets threaded on the inner loops further increases the compressive force exerted by the coil device 614 on the tissue, eventually causing a desired septal defect between the left and the right atriums of the heart.

FIG. 7 is a flowchart illustrating the steps of using a coiled SMA wire for creating a septal defect in a human heart, in accordance with an embodiment of the present specification. At step 702, in order to form a septal defect or shunt between a first chamber and a second chamber of a heart, firstly, a wall/septum between the two chambers is identified. At step 704, the septum between the identified chambers is pierced by using a needle encased in a catheter positioned in the right heart chamber to obtain a trans-septal puncture. At step 706, a coiled SMA wire having magnets threaded on adjacent inner loops (such as shown in FIG. 5A), wherein the diameter of outer loops is greater than that of inner loops, is deployed through the trans-septal puncture, such that approximately half of the coil is in the first chamber and approximately the other half is in the second chamber. During deployment, at step 708, the SMA wire changes from a substantially linear pre-deployment shape to a coiled post-deployment shape. At step 710, the inner loops of the coil compress due to the attractive forces between the magnets, causing pressure necrosis, and slowly cut through the septum forming a septal defect between the first and the second chambers of the heart. At step 712, the large diameter outer coil loops without the magnets anchor the coil in the septal defect preventing the coil from passing spontaneously or dislodging.

FIG. 8A illustrates a human heart 800 comprising a healthy mitral valve 802. FIG. 8B illustrates a human heart 801 suffering from a mitral valve 803 incompetence or a mitral prolapse condition. Referring to FIG. 8A, mitral valve 802 is located between left atrium 804 and left ventricle 806. The mitral valve 802 opens due to increased pressure as the left atrium 804 fills with blood, and allows blood to flow through into the left ventricle 806 as the heart expands (diastole). As the heart contracts (systole), the mitral valve 802 closes, thereby forcing blood 807 to flow into aorta 808. This process is vital to the heart's function. Mitral valve prolapse or incompetence occurs when the mitral valve does not close properly during systole. This may cause blood to leak the wrong way back into the left atrium, known as regurgitation, which leads to shortness of breath, palpitations, and chest pain. Referring to FIG. 8B, due to an incompetence or prolapse of mitral valve 803, blood 810 flows back into the left atrium 804 causing health problems.

Figure 9B:
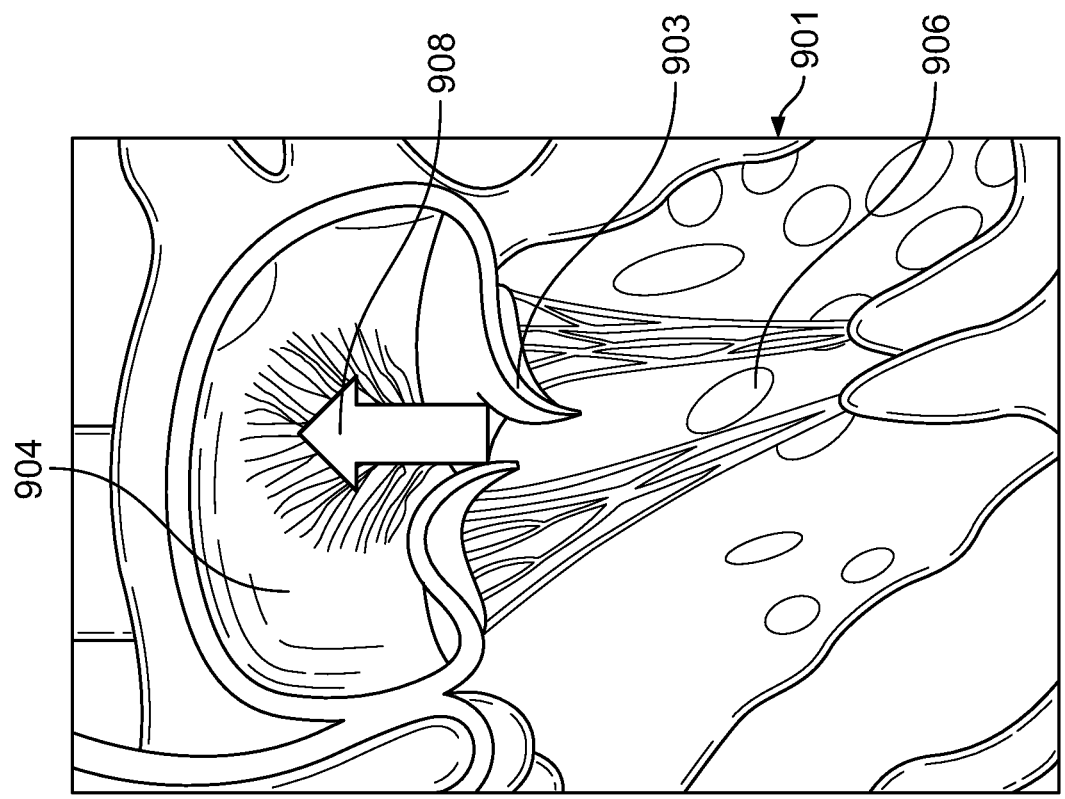
FIG. 9B illustrates a mitral valve in prolapse condition.
Figure 9A:
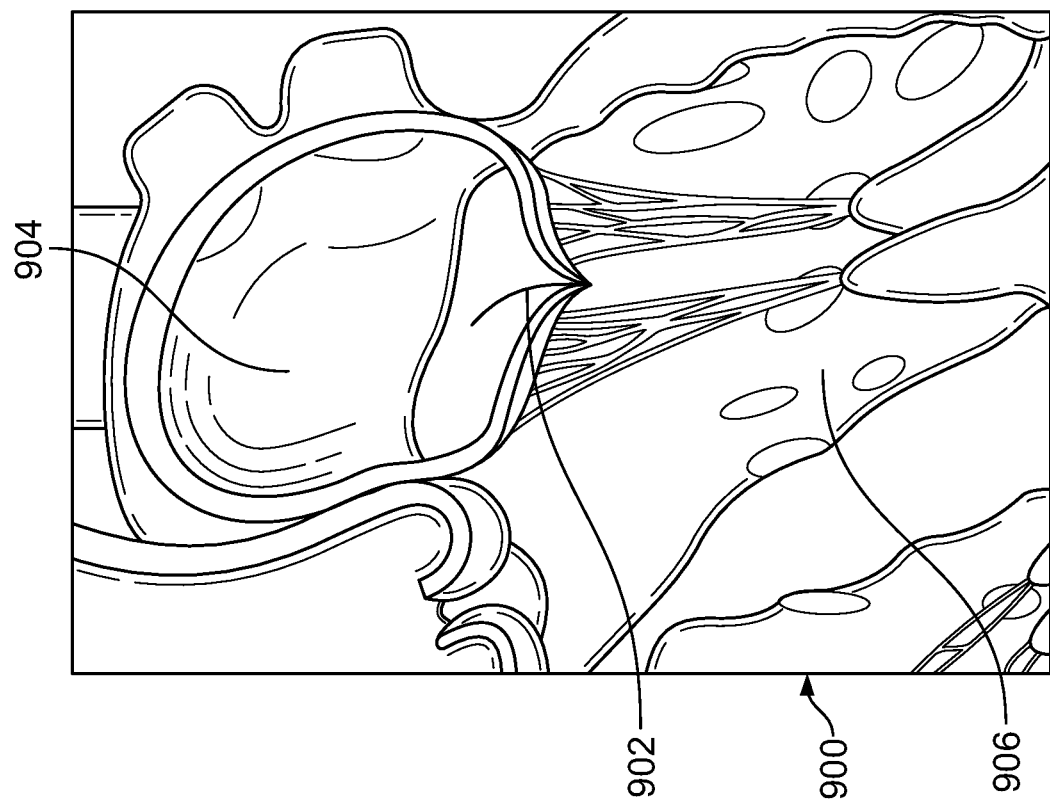
FIG. 9A illustrates a closed mitral valve in a human heart.
Figure 9D:
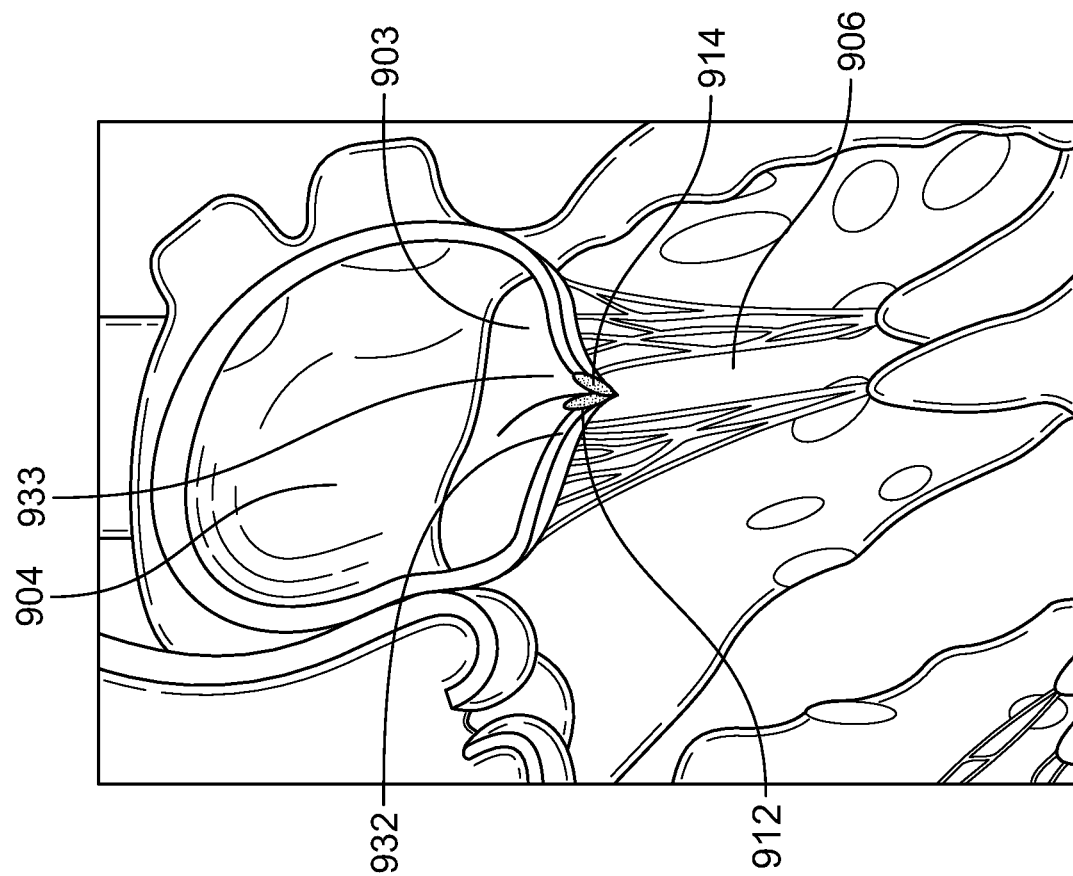
FIG. 9D illustrates the prolapsed mitral valve of FIG. 9C closed due to attractive forces between the magnets, in accordance with an embodiment of the present specification.
Figure 9C:
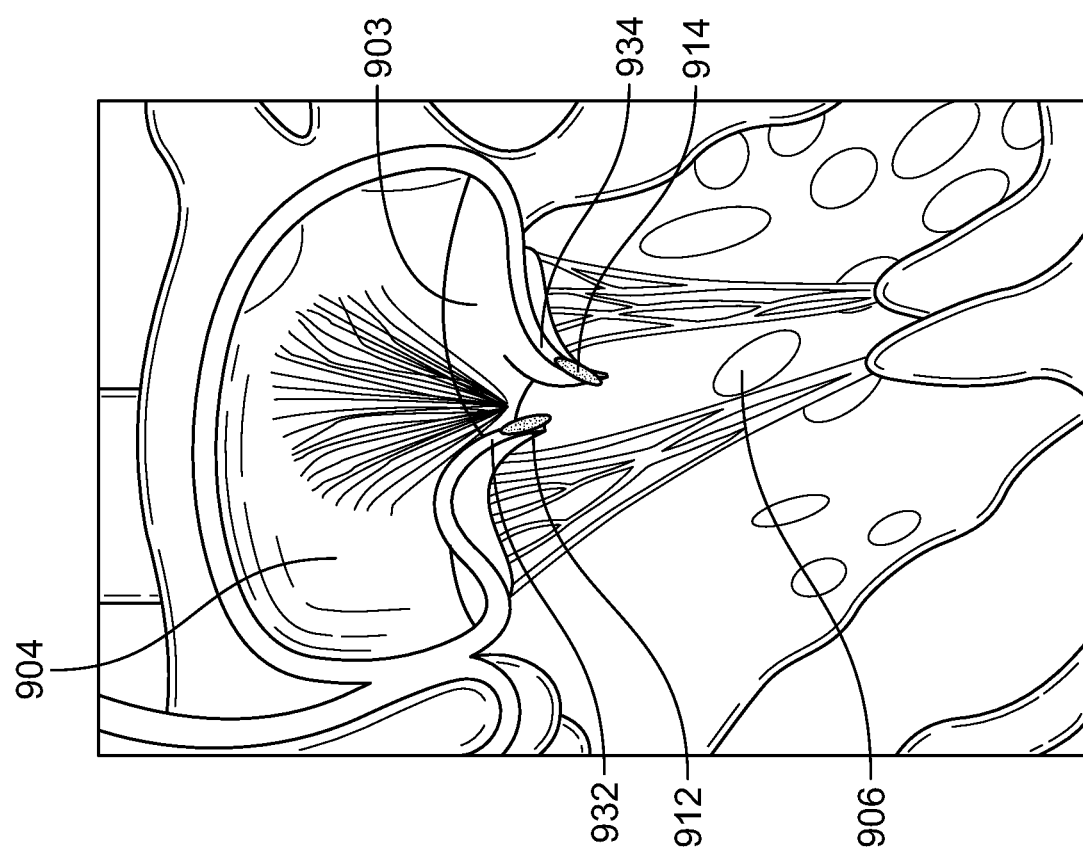
FIG. 9C illustrates a pair of magnets deployed on each leaflet of the prolapsed mitral valve shown in FIG. 9B, in accordance with an embodiment of the present specification.

FIG. 9A illustrates a closed healthy mitral valve 902 in a human heart 900. FIG. 9B illustrates a mitral valve 903 in a prolapse condition in a human heart 901. FIG. 9C illustrates a pair of magnets 912, 914 deployed on each leaflet 932, 934 of the prolapsed mitral valve 903 shown in FIG. 9B, in accordance with an embodiment of the present specification. FIG. 9D illustrates the prolapsed mitral valve 903 of FIG. 9C closed appropriately due to attractive forces between the magnets 912, 914, in accordance with an embodiment of the present specification. Referring to FIGS. 9A, 9B, 9C and 9D simultaneously, a healthy mitral valve 902 in a closed state separates a left atrium 904 of the heart from a left ventricle 906. In a prolapsed or incompetence condition, a prolapsed mitral valve 903 does not close properly, allowing blood 908 from the left ventricle 906 to regurgitate back into the left atrium 904 as the left ventricle 906 contracts. In an embodiment, as shown in FIG. 9C, a pair of magnets 912 and 914 are deployed on a left and right leaflet 932, 934 respectively of the prolapsed mitral valve 903. As the prolapsed mitral valve 903 begins to close, the attraction between the magnets 912, 914 increases, causing the leaflets 932, 934 of the valve 903 to come closer to one another, assisting the mitral valve 903 in closing substantially or completely and thereby eliminating the prolapsed condition. FIG. 9D illustrates the magnets 912, 914 in close proximity to one another with the leaflets 932, 933 in contact with each other and the mitral valve 903 closed. In various embodiments, the magnets 912, 914 comprises a single magnet, a plurality of magnets, or an SMA wire with magnets threaded thereon, as described in detail in FIGS. 10A through 11B. During forward flow, the pressure from flow on the leaflets 932, 933 separates the magnets 912, 914 and, as the distance between magnets 912, 914 increases, the attraction force exponentially decreases, allowing the valve to open for forward flow. Therefore, the valve defect device does not produce any significant impairment of valvular function during forward flow, but rather preferentially reduces reverse or back flow through valve 903.

In an embodiment, a magnet coupled with a proximal end of a straight/linear SMA wire is delivered to each leaflet of a prolapsed mitral valve. A distal end of the SMA wire comprises a sharp end for puncturing into the mitral valve leaflet. After piercing, due to body heat, the straight/linear SMA wire coils up, i.e. changes shape to a non-linear configuration, thereby anchoring the magnet to the leaflet. FIG. 10A illustrates an SMA coil with at least one magnet being delivered to a mitral valve leaflet, in accordance with an embodiment of the present specification. A catheter 1002 is advanced through an inferior vena cava 1001 and used to puncture a septum of a heart 1004 and deliver an SMA wire coupled at a proximal end to a magnet to leaflets of a mitral valve 1006. FIG. 10B illustrates leaflets 1005, 1007 of the mitral valve 1006 closed due to attraction between the magnets of SMA wire and magnet devices 1008, 1010, in accordance with an embodiment of the present specification. FIG. 10C illustrates an SMA wire 1012 coupled with a magnet 1010, in accordance with an embodiment of the present specification. Magnet 1010 is coupled with a proximal end of the SMA wire 1012. Distal end of the SMA wire 1012 comprises a sharp point 1014 for piercing a mitral valve leaflet for anchoring the magnet 1010 therein. In some embodiments, magnet 1010 includes a threaded opening at its proximal end for coupling with a delivery device as described with reference to FIG. 13. In other embodiments, the SMA wire 1012 includes a separate connecting component at its proximal end for coupling with the delivery device depicted in FIG. 13. FIGS. 10D, 10E, and 10F illustrate random post-deployment configurations 1016, helical post-deployment configurations 1018, and spiral configurations 1020 respectively, of an SMA wire upon being delivered at a deployment site, in accordance with embodiments of the present specification.

In embodiments, magnets threaded in SMA wires may be used to treat valve dysfunction in various portions of the heart. FIG. 11A illustrates a heart 1100 depicting a myocardium 1101 and fibrous skeleton 1103 and showing a plurality of heart valves closed by using magnets threaded in SMA wires. As shown in FIG. 11A, valve dysfunctions in mitral valve 1102, tricuspid valve 1104, aortic valve 1106, pulmonary valve 1108 may all be treated by using devices comprising magnets threaded on an SMA wire 1112, 1114, 1116, 1118 respectively, deployed at the valve site. FIG. 11B illustrates a portion of an SMA wire/magnet device, comprising a magnet threaded on an SMA wire, deployed at a valve site, in accordance with an embodiment of the present specification. Magnet 1120 is threaded on a first portion of SMA wire 1122, which pierces a valve leaflet 1124 such that the magnet 1120 rests on one side of the leaflet 1124 and a second portion of the SMA wire 1126, coiled due to body heat, rests on a second side of the leaflet 1124. Referring to FIGS. 9C through 11B, as the valve starts to close, the magnets come closer and the attraction force between them increases exponentially, closing the valve. As the valve starts to open, the distance between the magnets increases and the attraction forces between them decrease exponentially, allowing the valve to open easily.

Figure 12:
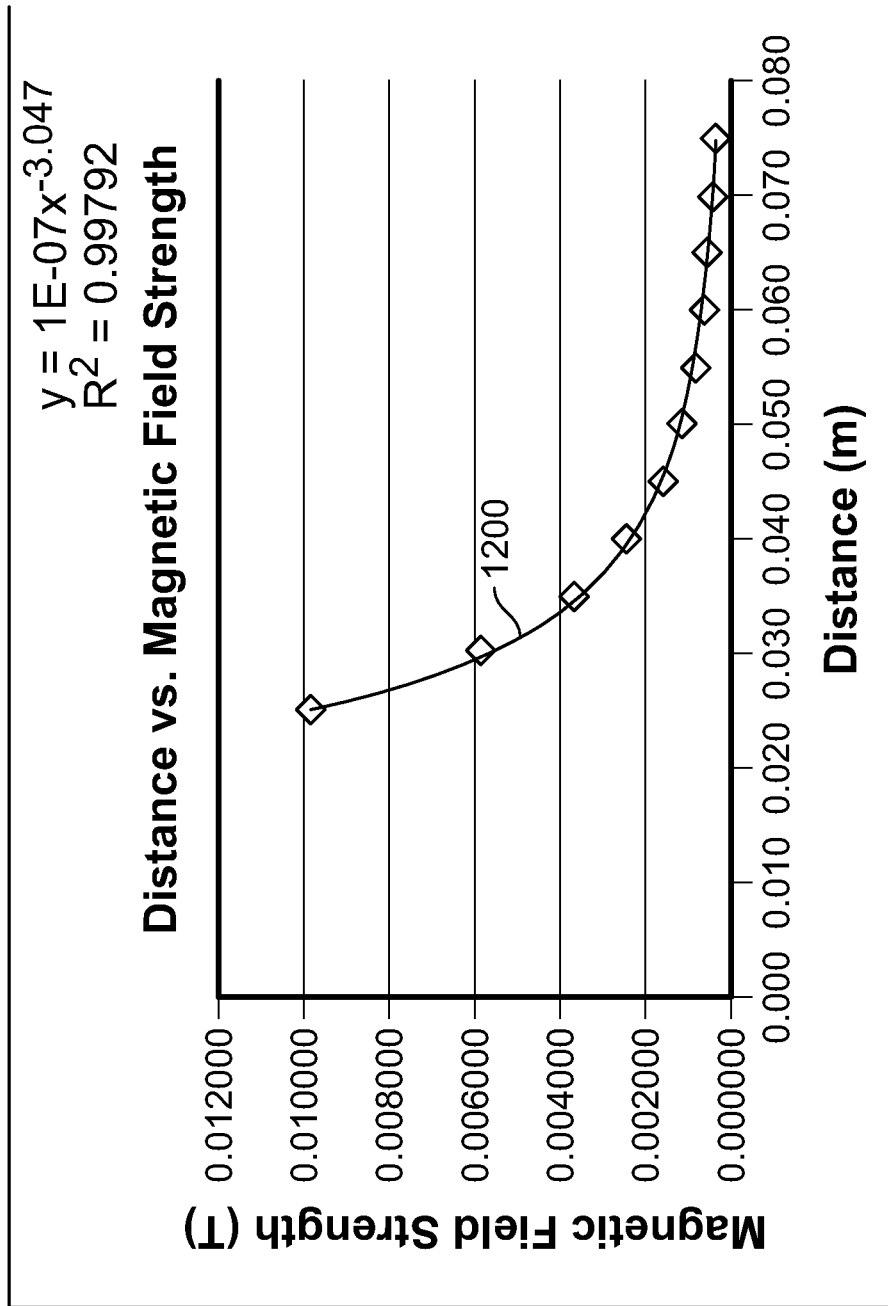
FIG. 12 illustrates a graph showing the exponential relationship between the distance and magnetic force between magnets, in accordance with an embodiment of the present specification.

FIG. 12 illustrates a graph showing the exponential relationship between the distance and magnetic force between magnets, in accordance with an embodiment of the present specification. Curve 1200 represents the magnetic field strength which decreases exponentially with increasing distance, as shown in FIG. 12. Referring to FIG. 10B, as the valve leaflets 1005, 1007 come together, the magnetic strength between the two magnets of the two SMA wire and magnet devices 1008, 1010 increases exponentially, keeping the valve 1006 shut and preventing regurgitation. When the forward blood flow opens the valve 1006, the magnetic force between the two magnets 1008, 1010 decreases exponentially and the valve leaflets, open allowing for forward blood flow.

Figure 13:
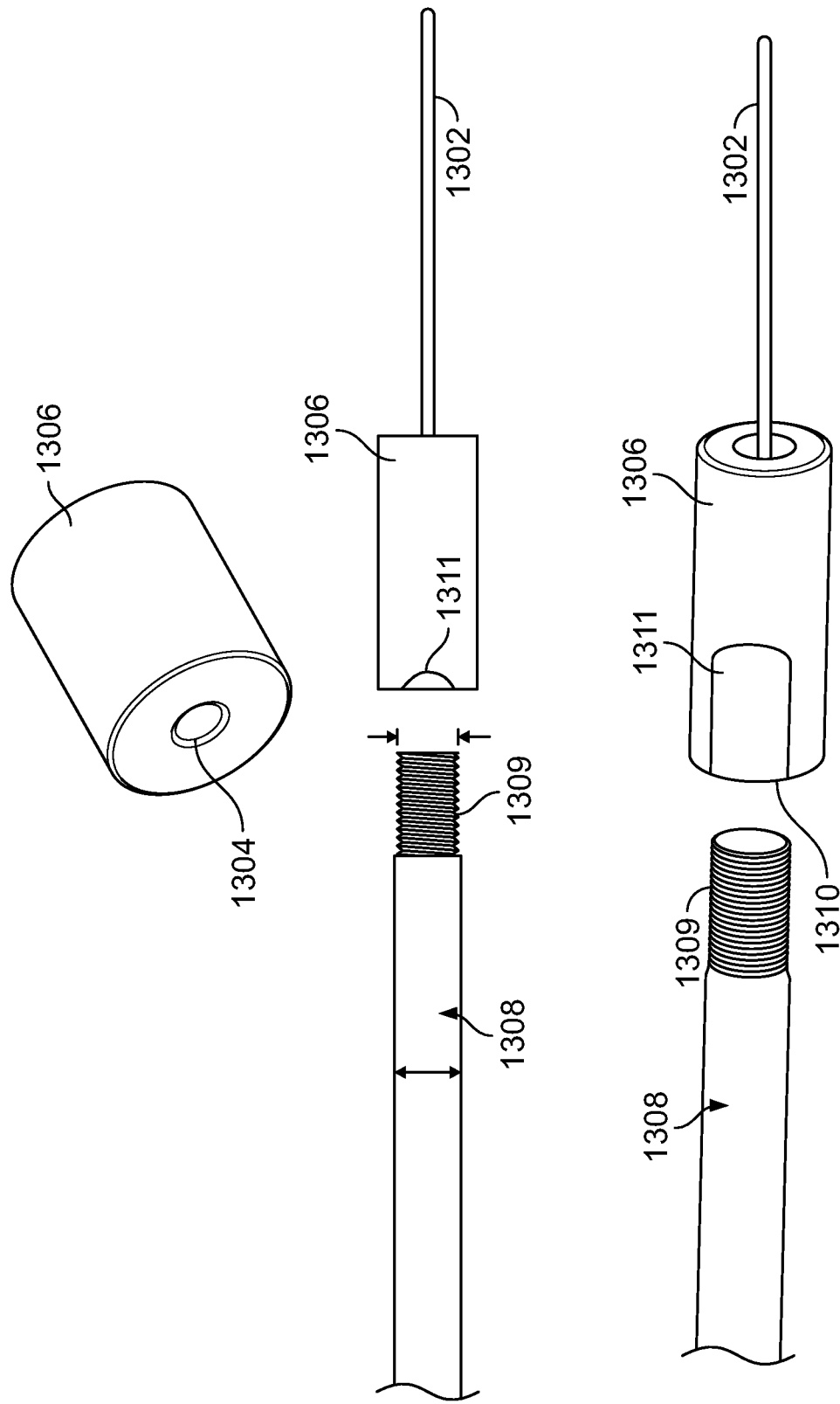
FIG. 13 illustrates a magnet threaded on an SMA wire to be deployed within a body via a push catheter, in accordance with an embodiment of the present specification.

FIG. 13 illustrates a magnet 1306 threaded on an SMA wire 1302 to be deployed within a body via a push catheter 1308, in accordance with an embodiment of the present specification. A linear SMA wire 1302 is threaded through an orifice 1304 of a cylindrical shaped magnet 1306. During deployment within a body, a pusher catheter 1308 is coupled with a proximal end 1310 of an SMA wire and magnet device. In an embodiment, the pusher 1308 includes a threaded distal end 1309 for coupling with the proximal end 1310 of the SMA wire and magnet device. In embodiments, the proximal end of the SMA wire and magnet device includes a threaded opening for receiving and coupling with the threaded distal end 1309 of the SMA wire and magnet device. Once the SMA wire and magnet device is delivered, the pusher 1308 is disengaged from the device by rotating the pusher 1308 in a counter clockwise direction to remove the distal end 1309 of the pusher from the proximal end of the SMA wire and magnet device. In one embodiment, the most proximate magnet 1306 couples with the pusher 1308 and includes a threaded opening at its proximal end for engaging with the distal end of the pusher 1308. In other embodiments, the SMA wire and magnet device includes a separate connecting component at its proximal end for coupling with the pusher 1308. In an embodiment, a diameter of the cylindrical magnet 1306 is approximately 2.5 mm, and a diameter of the orifice 1304 is approximately 0.9 mm. In an embodiment, a length of the cylindrical magnet 1306 is approximately 2.5 mm. In various embodiments, the delivery device comprising a pusher catheter 1308 of FIG. 13 can be used to deploy either the shunt creating devices disclosed in the present specification (for example, depicted with reference to FIGS. 3A-6B and 14A-16B) or the valve defect devices disclosed in the present specification (for example, with reference to FIGS. 8A-11B).

FIGS. 14A, B, C, and D illustrate another example of a Shape Memory Alloy (SMA) coil and magnet device 1400 that may be used to create a septal defect, in accordance with embodiments of the present specification. FIG. 14A is a side view of the SMA coil and magnet device 1400. FIG. 14B is a cross-sectional view of the SMA coil and magnet device 1400 of FIG. 14A. FIG. 14C is a top-down view of the SMA coil and magnet device 1400 of FIG. 14A. FIG. 14D is a perspective view of the SMA coil and magnet device 1400 of FIG. 14A. Referring together to FIGS. 14A, B, C, and D, coil 1400 comprises two inner loops 1402. Inner loops 1402 are threaded with magnets 1404 interspersed with spacers 1406. The two ends of the inner loops 1402 are extended to two corresponding outer loops 1408 and 1410. In an embodiment, outer loop 1408 is positioned at a proximal end of a wall of a first organ or tissue portion, and may be referred to as proximal outer loop 1408. In an embodiment, outer loop 1410 is positioned at a distal end beyond a wall of a second organ or tissue portion, and may be referred to as distal outer loop 1410. In embodiments, outer loops 1408 and 1410 have a diameter that is greater than a diameter of inner loops 1402. In an embodiment, the outer loops have a diameter of 34 mm and the inner loops have a diameter of 18.5 mm when measured from an outer surface of the magnets on the inner loops and 16 mm when measured from the SMA wire of the inner loops. In an embodiment, a width of coil 1400 is approximately 7.3 mm and a thickness of the SMA wire 1401 of the device 1400 is approximately 0.6 mm. In an embodiment, a diameter of the magnets 1404 is approximately 2.5 mm. In various embodiments, spacers 1406 comprise silicone or Nitinol tubes or O-rings or circular balls. In some embodiments, in order to assist with proper placement, the spacers 1406 are colored differently depending on which side of the created septal defect they will be deployed. In an embodiment, referring to FIG. 14A, spacers 1406*p* are configured to be positioned on a proximal side of the septal defect and are a first color, for example, red, while spacers 1406*d* are configured to be positioned on a distal side of the septal defect and are a second color, for example, black.

In embodiments of the present specification, outer loops 1408 and 1410 are comprised of a non-linear wire. In one embodiment, outer loops 1408 and 1410 are comprised of a wire that is structured like a wave, for example a sine wave, such that the troughs of the wave are positioned near the inner loops 1402, and have an approximate diameter of 18.5 mm, and the crests of the wave are positioned away from the inner loops. The wave structure enhances anchoring function by providing more points of contact of the wire with the body tissue than a simple loop. Accordingly, it is preferred for each outer loop to have a varying radius, thereby forming a circle with a wave-like perimeter. In an embodiment, diameter of the loop measured at the crests of outer loops 1408 and 1410 is 34 mm. In an embodiment, the angle formed between consecutive crests of each loop is 60°, resulting in 6 crests (nodes) in each outer loop 1408 and 1410. In an alternative embodiment, the angle between consecutive crests is 90°, providing 4 crests in each outer loop 1408 and 1410. In another alternative embodiment, the angle between consecutive crests is 120°, providing 3 crests in each outer loop 1408 and 1410. In embodiments, the angle between consecutive crests may range from 15° to 180°.

In embodiments, each outer loop 1408 and 1410 is positioned such that the loops stagger in a manner that each crest of outer loop 1408 corresponds to each trough of outer loop 1410, and vice-versa, when viewed from the top (see FIG. 14C). This configuration allows for greater stability by staggering the contact points of the outer loops on each side of the tissue (for example, atrial septum), distributing the pressure applied by the coil to the body tissue move evenly to support the device in place. In addition, staggering the nodes prevents pinching of the tissue at the same point from both sides, which could inadvertently lead to tissue necrosis, resulting in unwanted increase in the size of the shunt and passage of the device.

In embodiments, tip of proximal outer loop 1408 includes a crimped probe 1412. Additionally, tip of distal outer loop 1410 includes a welded cautery probe 1414. Crimped probe 1412 may include a screw (threaded end) to ease connection with a delivery device and deployment at the proximal end of the wall of the first organ or tissue portion. In an embodiment, a diameter of the screw head of crimped probe 1412 is approximately 1.5 mm, whereas the diameter of the crimped tip of the screw within crimped probe 1412 is approximately 1.3 mm. Cautery tip 1414 may enable puncture at the distal end through the wall of the first organ or tissue portion (for example, atrial septum). In an embodiment, the tip of cautery probe 1414 has a diameter of approximately 2.67 mm.

FIGS. 15A, B, C, and D illustrate another example of a Shape Memory Alloy (SMA) coil and magnet device 1500 that includes at least two wires braided together, which may be used to create a septal defect, in accordance with embodiments of the present specification. FIG. 15A is a side view of the SMA coil and magnet device 1500. FIG. 15B is a cross-sectional view of the SMA coil and magnet device 1500 of FIG. 15A. FIG. 15C is a top-down view of the braided SMA coil and magnet device 1500 of FIG. 15A. FIG. 15D is a perspective view of the braided SMA coil and magnet device 1500 of FIG. 15A. Referring together to FIGS. 15A, B, C, and D, coil 1500 comprises two inner loops 1502. Inner loops 1502 are threaded with magnets 1504 interspersed with spacers 1506. The two ends of the inner loops 1502 are extended to two corresponding outer loops 1508 and 1510. In an embodiment, outer loop 1508 is positioned at a proximal end of a wall of a first organ or tissue portion, and may be referred to as proximal outer loop 1508. In an embodiment, outer loop 1510 is positioned at a distal end beyond a wall of a second organ or tissue portion (for example, atrial septum), and may be referred to as distal outer loop 1510. In embodiments, outer loops 1508 and 1510 have a diameter that is greater than a diameter of inner loops 1502. In an embodiment, the outer loops have a diameter of 34 mm, and the inner loops have a diameter of 18.5 mm when measured from an outer surface of the magnets on the inner loops and 16 mm when measured from the SMA wire of the inner loops. In an embodiment, a width of coil 1500 is approximately 7.3 mm and a thickness of each SMA wire 1501 of the device 1500 is approximately 0.6 mm, for a combined thickness of adjacent braided wires of approximately 1.2 mm. In an embodiment, a diameter of the magnets 1504 is approximately 2.5 mm. In various embodiments, spacers 1506 comprise silicone or Nitinol tubes or O-rings or circular balls.

In embodiments of the present specification, outer loops 1508 and 1510 are comprised of a non-linear combined wire 1516. In embodiments, the device 1500 includes a combined wire 1516 which comprises at least two wires 1501 that are combined with each other, such as by braiding. The additional wire(s) provides added support to outer loops 1508 and 1510, thereby making them stronger. Providing additional wires increases the strength of the outer coil without causing too much strain in the wire. Increasing the thickness or diameter of the wire would result in a higher strain when changing the wire from a loop shape to a straight shape. To accommodate a thicker wire, the diameter of the loop would need to be increased. By using two wires, the strength of the coil is increased without needing to increase the diameter of the loop. In one embodiment, outer loops 1508 and 1510 are comprised of braided wire 1516 that is structured like a wave, for example a sine wave, such that the troughs of the wave are positioned near the inner loops 1502, and have an approximate diameter of 18.5 mm, and the crests of the wave are positioned away from the inner loops. In an embodiment, diameter of the loop measured at the crests of outer loops 1508 and 1510 is 34 mm. In an embodiment, the angle formed between consecutive crests of each loop is 60°, resulting in 6 crests (nodes) in each outer loop 1508 and 1510. In an alternative embodiment, the angle between consecutive crests is 90°, providing 4 crests in each outer loop 1508 and 1510. In another alternative embodiment, the angle between consecutive crests is 120°, providing 3 crests in each outer loop 1508 and 1510. In embodiments, the angle between consecutive crests may range from 15° to 180°.

In embodiments, each outer loop 1508 and 1510 is positioned such that the loops stagger in a manner that each crest of outer loop 1508 correspond to each trough of outer loop 1510, and vice-versa, when viewed from the top (see FIG. 15C). As noted above, this configuration allows for greater stability by staggering the contact points of the outer loops on each side of the tissue (for example, atrial septum) to support the device in place. In addition, staggering the nodes prevents pinching of the tissue at the same point from both sides, which could inadvertently lead to tissue necrosis, resulting in unwanted increase in the size of the shunt and passage of the device.

In embodiments, tip of proximal outer loop 1508 includes a crimped probe 1512. Additionally, tip of distal outer loop 1510 includes a welded cautery probe 1514. Crimped probe 1512 may include a screw (threaded end) to ease connection with a delivery device and deployment at the proximal end of the wall of the first organ or tissue portion. In an embodiment, a diameter of the screw head of crimped probe 1512 is approximately 1.5 mm, whereas the diameter of the crimped tip of the screw within crimped probe 1512 is approximately 1.3 mm. Cautery tip 1514 may enable puncture at the distal end through the wall of the second organ or tissue portion (for example, atrial septum). In an embodiment the tip of cautery probe 1514 has a diameter of approximately 2.67 mm.

Figure 16A:
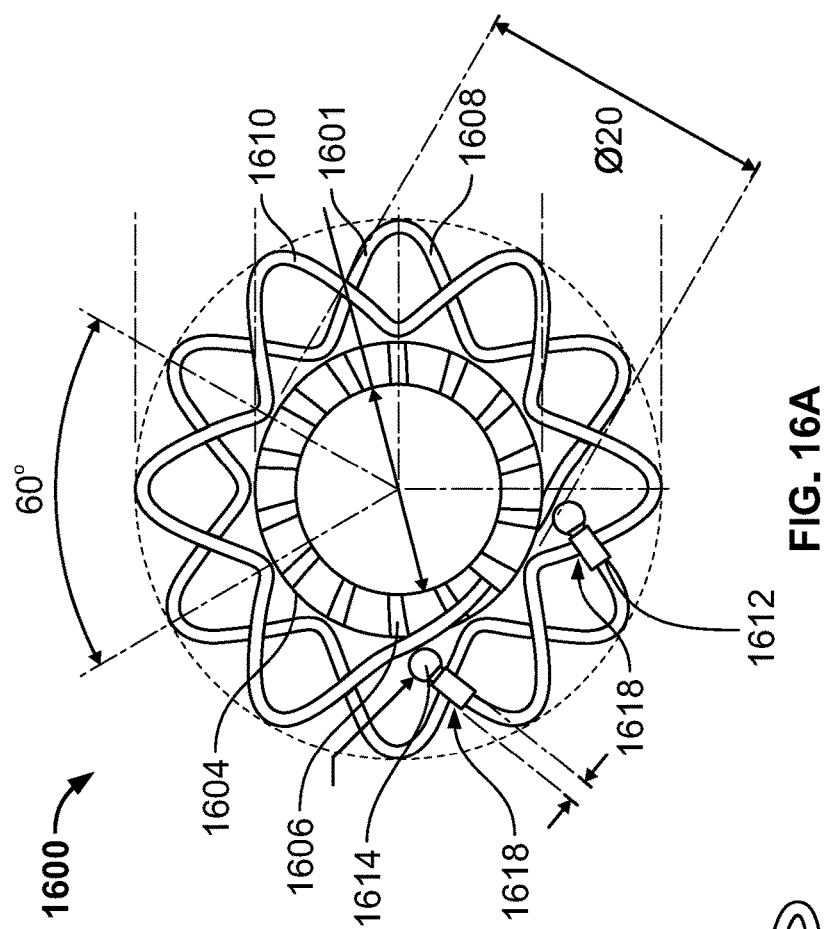
FIG. 16A illustrates a top-down view of a device for creating a septal defect and comprising an SMA wire with a plurality of magnets and cautery probes, in accordance with an embodiment of the present specification.
Figure 16B:
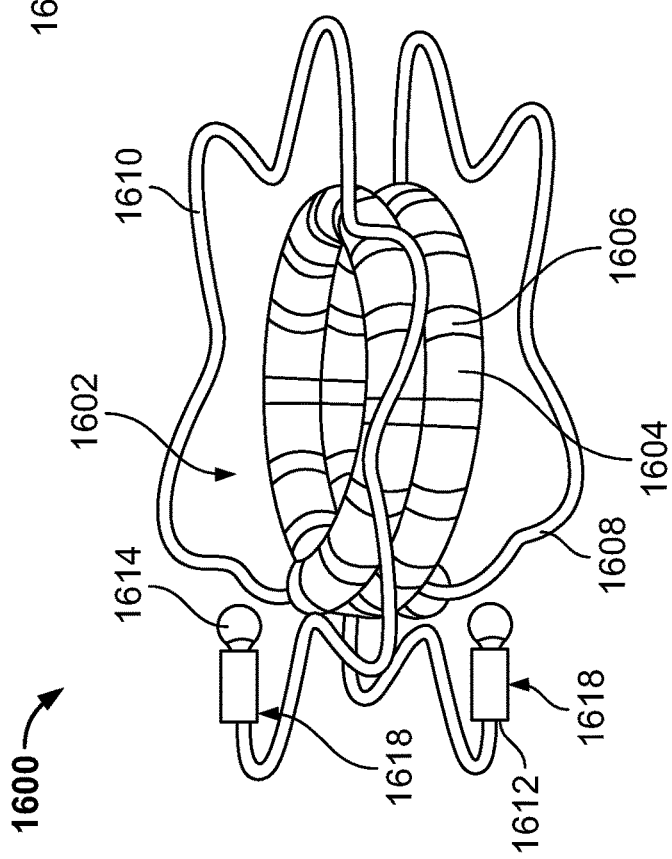
FIG. 16B illustrates a perspective view of the device for creating a septal defect of FIG. 16A.

FIGS. 16A and B illustrate another example of a Shape Memory Alloy (SMA) coil and magnet device 1600 that includes cautery probes and screws at both tips of outer loops 1608 and 1610, which may be used to create a septal defect, in accordance with embodiments of the present specification. FIG. 16A is a top-down view of the SMA coil and magnet device 1600. FIG. 16B is a perspective view of the SMA coil and magnet device 1600 of FIG. 16A. Referring together to FIGS. 16A and B, coil 1600 comprises two inner loops 1602. Inner loops 1602 are threaded with magnets 1604 interspersed with spacers 1606. The two ends of the inner loops 1602 are extended to two corresponding outer loops 1608 and 1610. In an embodiment, outer loop 1608 is positioned at a proximal end of a wall of a first organ or tissue portion, and may be referred to as proximal outer loop 1608. In an embodiment, outer loop 1610 is positioned at a distal end beyond a wall of a second organ or tissue portion (for example, atrial septum), and may be referred to as distal outer loop 1610. In embodiments, outer loops 1608 and 1610 have a diameter that is greater than a diameter of inner loops 1602. In an embodiment, the outer loops have a diameter of 34 mm, and the inner loops have a diameter of 18.5 mm when measured from an outer surface of the magnets on the inner loops and 16 mm when measured from the SMA wire of the inner loops. In an embodiment, a width of coil 1600 is approximately 7.3 mm and a thickness of the SMA wire 1601 of the device 1600 is approximately 0.6 mm. In an alternative embodiment, coil 1600 includes at least two wires braided together, in which case a thickness of the SMA wires braided together and forming outer loops 1608 and 1610 of coil 1600 is approximately 1.2 mm. In an embodiment, a diameter of the magnets 1604 is approximately 2.5 mm. In various embodiments, spacers 1606 comprise silicone or Nitinol tubes or O-rings or circular balls.

In embodiments of the present specification, outer loops 1608 and 1610 are comprised of a non-linear wire. In one embodiment, outer loops 1608 and 1610 are comprised of a wire that is structured like a wave, for example a sine wave, such that the troughs of the wave are positioned near the inner loops 1602, and have an approximate diameter of 18.5 mm, and the crests of the wave are positioned away from the inner loops. In an embodiment, diameter of the loop measured at the crests of outer loops 1608 and 1610 is 34 mm. In an embodiment, the angle formed between consecutive crests of each loop is 60°, resulting in 6 crests (nodes) in each outer loop 1608 and 1610. In an alternative embodiment, the angle between consecutive crests is 90°, providing 4 crests in each outer loop 1608 and 1610. In another alternative embodiment, the angle between consecutive crests is 120°, providing 3 crests in each outer loop 1608 and 1610. In embodiments, the angle between consecutive crests may range from 15° to 180°.

In embodiments, each outer loop 1608 and 1610 is positioned such that the loops stagger in a manner that each crest of outer loop 1608 correspond to each trough of outer loop 1610, and vice-versa, when viewed from the top (see FIG. 16A). As noted above, this configuration allows for greater stability by staggering the contact points of the outer loops on each side of the tissue (for example, atrial septum) to support the device in place. In addition, staggering the nodes prevents pinching of the tissue at the same point from both sides, which could inadvertently lead to tissue necrosis, resulting in unwanted increase in the size of the shunt and passage of the device.

In embodiments, tips of proximal and distal outer loops 1608 and 1610 each include a screw 1612 encompassed in a magnet 1618. Additionally, tip of screws 1612 are connected to cautery probes 1614. Screws 1612 may ease deployment at the proximal end of the wall of the first organ or tissue portion as well as at the distal end beyond the wall of the second organ or tissue portion. Cautery probes 1614 may ease puncture of the corresponding locations for deployment.

Screw 1612 may be partially or wholly encompassed in a first magnet 1618. Screw 1612 may ease connection with a delivery device and deployment at the proximal end of the wall of the first organ or tissue portion. Cautery tip 1614 may also be partially encompassed in a second magnet 1618. Cautery tip 1614 may enable puncture at the distal end beyond the wall of the second organ or tissue portion. In embodiments, encompassing magnets 1618 align with and attach themselves to magnets 1604 in the inner loops 1602 of coil 1600. The attaching mechanism of the magnets enables locking of the wire of outer loops 1608 and 1610 back to coil 1600.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A method for treating a patient's heart condition, the method comprising:
    using a member having a sharp tip positioned in a catheter, piercing a portion of the heart chamber;
    delivering a wire proximate said portion of the heart chamber, wherein:
        the wire comprises a shape memory alloy;
        the wire is adapted to transform from a substantially straight wire to a coil shape wire upon an increase in temperature;
        the wire, upon transforming to the coil shape, comprises at least two inner loops and at least two outer loops;
        a diameter of at least one of the at least two inner loops is less than a diameter of at least one of the at least two outer loops;

the wire, when in the coil shape, is adapted to exert a compressive force upon layers of tissue caught between the at least two inner loops; and a plurality of magnets, coupled to the at least two inner loops, wherein the plurality of magnets are adapted to provide a compressive force to adjacent inner loops of the wire in the coil shape.

2. The method of claim 1 further comprising delivering heat to the wire to transform the substantially straight wire to the coil shape wire using an energy source adapted to be connected to an end of the wire.

3. A method for treating a valve defect in a patient's body, the method comprising:

delivering a device into the patient's body, wherein the device comprises a wire made of a shape memory alloy, wherein the wire has a first part, comprising a first end, and a second part, comprising a second end, wherein a first magnet is attached to the first part, wherein a second magnet is attached to the second part, and wherein the wire is adapted to transform from a substantially straight shape to a substantially coiled shape upon an increase in temperature;

using the first end, piercing a first leaflet of the valve in order to create contact between the first magnet and the first leaflet; and using the second end, piercing a second leaflet of the valve in order to create contact between the second magnet and the second leaflet, wherein attractive forces between the first magnet and the second magnet cause a closure of the valve to prevent or reduce back flow through the valve.

4. The method of claim 3 further comprising delivering heat to the wire to transform the substantially straight wire to the coil shape wire using an energy source adapted to be connected to an end of the wire.

* * * * *